United States Patent
Hirohama et al.

(10) Patent No.: US 10,694,980 B2
(45) Date of Patent: Jun. 30, 2020

(54) EXERCISE SUPPORT DEVICE, EXERCISE SUPPORT METHOD AND EXERCISE SUPPORT PROGRAM

(71) Applicant: CASIO COMPUTER CO., LTD., Shibuya-ku, Tokyo (JP)

(72) Inventors: Masayuki Hirohama, Fussa (JP); Ryohei Yamamoto, Tachikawa (JP); Mitsuyasu Nakajima, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 259 days.

(21) Appl. No.: 15/187,197

(22) Filed: Jun. 20, 2016

(65) Prior Publication Data

US 2016/0367853 A1    Dec. 22, 2016

(30) Foreign Application Priority Data

Jun. 22, 2015   (JP) .................................. 2015-124902

(51) Int. Cl.
*A61B 5/11* (2006.01)
*G01S 19/19* (2010.01)
(Continued)

(52) U.S. Cl.
CPC .............. *A61B 5/112* (2013.01); *G01S 19/19* (2013.01); *G06K 9/00342* (2013.01);
(Continued)

(58) Field of Classification Search
CPC ............ G06K 9/00342; G06K 9/00348; A61B 5/112; A61B 5/121
See application file for complete search history.

(56) References Cited

U.S. PATENT DOCUMENTS

| 6,684,090 B2 | 1/2004 | Ali et al. |
| 6,996,427 B2 | 2/2006 | Ali et al. |

(Continued)

FOREIGN PATENT DOCUMENTS

| JP | 2002263086 A | 9/2002 |
| JP | 2004358229 A | 12/2004 |

(Continued)

OTHER PUBLICATIONS

Japanese Office Action (and English language translation thereof) dated Apr. 17, 2019 issued in Japanese Application No. 2015-124902.

*Primary Examiner* — Eddy Saint-Vil
*Assistant Examiner* — William D Ermlick
(74) *Attorney, Agent, or Firm* — Holtz, Holtz & Volek PC

(57) ABSTRACT

An exercise support device and an exercise support method are provided by which a judgment regarding the landing of the left and right feet of a user can be accurately made with low power consumption, so that the user can appropriately grasp and judge the balance of the use of the body in an exercise. First, based on changes in acceleration in a vertical direction with respect to the ground which has been acquired by a sensor section worn on the body during a running exercise, landing timing at which one of the left and right feet is landed is detected. Then, based on whether a difference between angular velocities around a traveling direction axis immediately after the latest landing timing and the preceding landing timing has a positive or negative value, whether the landed foot is the left foot or the right foot is judged.

17 Claims, 17 Drawing Sheets

(51) Int. Cl.
*G06K 9/00* (2006.01)
*A61B 5/00* (2006.01)

(52) U.S. Cl.
CPC .......... *A61B 5/1112* (2013.01); *A61B 5/6831* (2013.01); *A61B 5/6838* (2013.01); *A61B 2503/10* (2013.01)

(56) References Cited

U.S. PATENT DOCUMENTS

| | | | |
|---|---|---|---|
| 7,024,233 B2 | 4/2006 | Ali et al. | |
| 7,753,861 B1* | 7/2010 | Kahn | A61B 5/1118 482/8 |
| 8,046,040 B2 | 10/2011 | Ali et al. | |
| 9,636,055 B2 | 5/2017 | Ali et al. | |
| 9,875,400 B2* | 1/2018 | Uchida | G09B 19/0038 |
| 10,130,289 B2 | 11/2018 | Ali et al. | |
| 2002/0035315 A1 | 3/2002 | Ali et al. | |
| 2004/0133087 A1 | 7/2004 | Ali et al. | |
| 2005/0033128 A1 | 2/2005 | Ali et al. | |
| 2006/0020177 A1* | 1/2006 | Seo | A61B 5/222 600/300 |
| 2006/0195025 A1 | 8/2006 | Ali et al. | |
| 2010/0132464 A1* | 6/2010 | Yasuhara | A61B 5/1038 73/504.12 |
| 2011/0054809 A1* | 3/2011 | Templeman | A61B 5/1118 702/44 |
| 2012/0041316 A1 | 2/2012 | Ali et al. | |
| 2013/0041617 A1* | 2/2013 | Pease | A43B 3/0005 702/139 |
| 2013/0090574 A1* | 4/2013 | Kuribayashi | A61B 5/1116 600/595 |
| 2013/0178958 A1* | 7/2013 | Kulach | A63B 24/0021 700/91 |
| 2013/0211474 A1* | 8/2013 | Nielsen | A61N 1/36003 607/49 |
| 2013/0274904 A1* | 10/2013 | Coza | G06F 3/011 700/91 |
| 2015/0081061 A1* | 3/2015 | Aibara | A61B 5/1122 700/91 |
| 2015/0081245 A1* | 3/2015 | Nagasaka | G01P 3/64 702/141 |
| 2016/0029954 A1* | 2/2016 | Sato | A61B 5/681 702/141 |
| 2016/0030804 A1* | 2/2016 | Mizuochi | A61B 5/11 482/8 |
| 2016/0030808 A1* | 2/2016 | Uchida | G06K 9/00342 482/8 |
| 2016/0038059 A1* | 2/2016 | Asada | A61B 5/1116 600/595 |
| 2016/0045140 A1* | 2/2016 | Kitamura | A61B 5/1116 600/595 |
| 2016/0379518 A1* | 12/2016 | Balakrishnan | A61B 5/0059 434/255 |
| 2017/0095692 A1* | 4/2017 | Chang | A63B 24/0003 |
| 2017/0325728 A1 | 11/2017 | Ali et al. | |
| 2018/0107867 A1* | 4/2018 | Uchida | G06K 9/00342 |

FOREIGN PATENT DOCUMENTS

| | | |
|---|---|---|
| JP | 2009160415 A | 7/2009 |
| JP | 2009261595 A | 11/2009 |
| JP | 2011251013 A | 12/2011 |
| JP | 2012179114 A | 9/2012 |
| JP | 2012205816 A | 10/2012 |
| JP | 2012248969 A | 12/2012 |
| JP | 2014094239 A | 5/2014 |
| JP | 2015058096 A | 3/2015 |
| JP | 2015058167 A | 3/2015 |

* cited by examiner (DISPLAY EXAMPLES)

169bpm : PITCH
180ms : FROM RIGHT-FOOT LANDING TO LEFT-FOOT LANDING
176ms : FROM LEFT-FOOT LANDING TO RIGHT-FOOT LANDING (a)

169bpm : PITCH
180ms : FROM RIGHT-FOOT LANDING TO LEFT-FOOT LANDING
176ms : FROM LEFT-FOOT LANDING TO RIGHT-FOOT LANDING (b)

TAP WHEN LEFT FOOT LANDS (c)

EXERCISE SUPPORT DEVICE, EXERCISE SUPPORT METHOD AND EXERCISE SUPPORT PROGRAM

CROSS-REFERENCE TO RELATED APPLICATION

This application is based upon and claims the benefit of priority from the prior Japanese Patent Application No. 2015-124902, filed Jun. 22, 2015, the entire contents of which are incorporated herein by reference.

BACKGROUND OF THE INVENTION

1. Field of the Invention

The present invention relates to an exercise support device, an exercise support method and an exercise support program by which the motion status (exercise status) of a human body at the time of exercise can be grasped so as to help the judgment and improvement of the motion status.

2. Description of the Related Art

In recent years, because of rising health consciousness, more and more people are performing daily exercises, such as running, walking, and cycling, to maintain their wellness or improve their health condition. In addition, an increasing number of people are aiming to participate in a race such as a marathon race through these daily exercises. These people are very conscious of and interested in measuring and recording various biological and exercise information so as to grasp their own health conditions and exercise status. The people aiming to participate in a race have an objective of achieving a successful record in the race, and therefore are very conscious of and interested in efficient and effective training methods.

On the other hand, many of these people have extremely less opportunities of receiving appropriate guidance on their own exercise methods, exercise forms, and the like from experts or instructors. Therefore, it is very difficult to grasp a balance in the use of the body at the time of their own exercise (for example, running exercise) and judge whether the balance is appropriate. Moreover, continuing exercise without keeping body balance is not only inefficient but also may cause damage to the body.

For example, in the judgment of a left-right balance in the use of the body at the time of a running exercise, it is important to make a judgment, based on an exercise index, as to whether various events measured during the running exercise are caused from the landing of the right foot or from the landing of the left foot. As a method for judging the landing of the right foot and the left foot, for example, Japanese Patent Application Laid-Open (Kokai) Publication No. 2011-251013 discloses a method where the judgment of the left and right legs constituting one footstep is made based on a direction (plus or minus direction) in which an angular velocity around a vertical axis at the time of walking, that is, a lateral rotation amount in the posture of the body wearing a sensor (measurement device) becomes maximum.

As for the motion of a human body in a running exercise, it is generally known that the rotation of the waist and the rotation of the chest around the vertical axis are in opposite directions. However, when the running speed is increased in the running motion, the rotation of the chest becomes larger than the rotation of the waist, and an intermediate point of rotation on the vertical axis (a center point where the rotating direction is switched) moves to a position near the waist. Accordingly, there is a problem in that, when a sensor device is worn on the waist and travels with the user to measure a motion in a running exercise, the wearing position of the sensor device is vertically shifted due to vibrations or the like in the running exercise, which makes it difficult to appropriately detect the rotation of the waist. As a result, the judgment of the landing of the left and right feet becomes unstable or incorrect.

Moreover, in the above-described method where a detection signal (or angular velocity data) from an angular velocity sensor is used to judge the landing of the left and right feet in a running exercise, the power consumption of the angular velocity sensor is often relatively large, which causes a problem in that the driving time of the sensor device may be affected (shortened).

SUMMARY OF THE INVENTION

An exercise support device according to one embodiment is disclosed. It comprises: at least one processor; and a memory storing instructions that, when executed by the at least one processor, control the at least one processor to: make a determination, by using a first component of sensor data acquired at certain timing that is determined based on landing timing at which one of a left foot and a right foot of a user is landed, whether a foot landed at the landing timing is the left foot of the user or the right foot of the user, the landing timing being determined by the sensor data, the sensor data being detected by a sensor that detects a motion status of the body of the user when the user travels, and outputs, as part of the sensor data corresponding to the motion status, angular velocity data of a rotating motion around a traveling direction of the user taken as a Y-axis; wherein the instructions further control the at least one processor to: make the determination by using at least the angular velocity data on the Y-axis outputted from the sensor as the first component of the sensor data.

An exercise support method according to one embodiment is disclosed. It comprises: making a determination, by using a first component of sensor data acquired at certain timing that is determined based on landing timing at which one of a left foot and a right foot of a user is landed, whether a foot landed at the landing timing is the left foot of the user or the right foot of the user, the landing timing being determined by the sensor data, the sensor data being detected by a sensor that detects a motion status of the body of the user when the user travels, and outputs, as part of the sensor data corresponding to the motion status, angular velocity data of a rotating motion around a traveling direction of the user taken as a Y-axis; wherein the method further comprising: making the determination by using at least the angular velocity data on the Y-axis outputted from the sensor as the first component of the sensor data.

A non-transitory computer-readable storage medium storing instructions according to one embodiment is disclosed. The instructions, when executed by at least one processor, control the processor to: make a determination, by using a first component of sensor data acquired at certain timing that is determined based on landing timing at which one of a left foot and a right foot of a user is landed, whether a foot landed at the landing timing is the left foot of the user or the right foot of the user, the landing timing being determined by the sensor data, the sensor data being detected by a sensor that detects a motion status of the body of the user when the user travels, and outputs, as part of the sensor data corresponding to the motion status, angular velocity data of a rotating motion around a traveling direction of the user taken as a Y-axis; wherein the instructions further control the at least one processor to: make the determination by using at least the angular velocity data on the Y-axis outputted from the sensor as the first component of the sensor data.

An exercise support system according to one embodiment is disclosed. It comprises: an exercise support device comprising: at least one processor; and a memory storing instructions that, when executed by the at least one processor, control the at least one processor to: make a determination, by using a first component of sensor data acquired at certain timing that is determined based on landing timing at which one of a left foot and a right foot of a user is landed, whether a foot landed at the landing timing is the left foot of the user or the right foot of the user, the landing timing being determined by the sensor data, the sensor data being detected by a sensor that detects a motion status of the body of the user when the user travels, and outputs, as part of the sensor data corresponding to the motion status, angular velocity data of a rotating motion around a traveling direction of the user taken as a Y-axis; wherein the instructions further control the at least one processor to: make the determination by using at least the angular velocity data on the Y-axis outputted from the sensor as the first component of the sensor data.

BRIEF DESCRIPTION OF THE DRAWINGS

The present invention can be more deeply understood by the detailed description below being considered together with the following drawings.

DETAILED DESCRIPTION OF THE PREFERRED EMBODIMENTS

Hereafter, embodiments of an exercise support device, an exercise support method, and an exercise support program according to the present invention will be described in detail. In the following descriptions of the embodiments, a case is described in which a user of the exercise support device according to the present invention performs a running exercise. However, the user may perform any other exercise, such as walking or cycling, as long as it is to cyclically and alternately move the left and right feet.

First Embodiment (Exercise Support Device)

Figure 1:
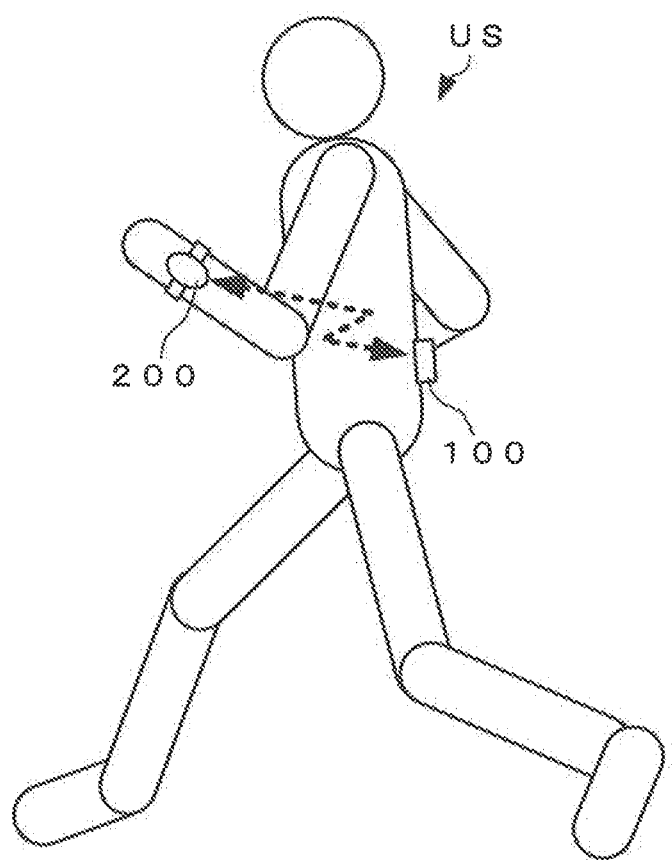
FIG. 1 is a schematic view of an exercise support device according to a first embodiment of the present invention.
Figure 2A:
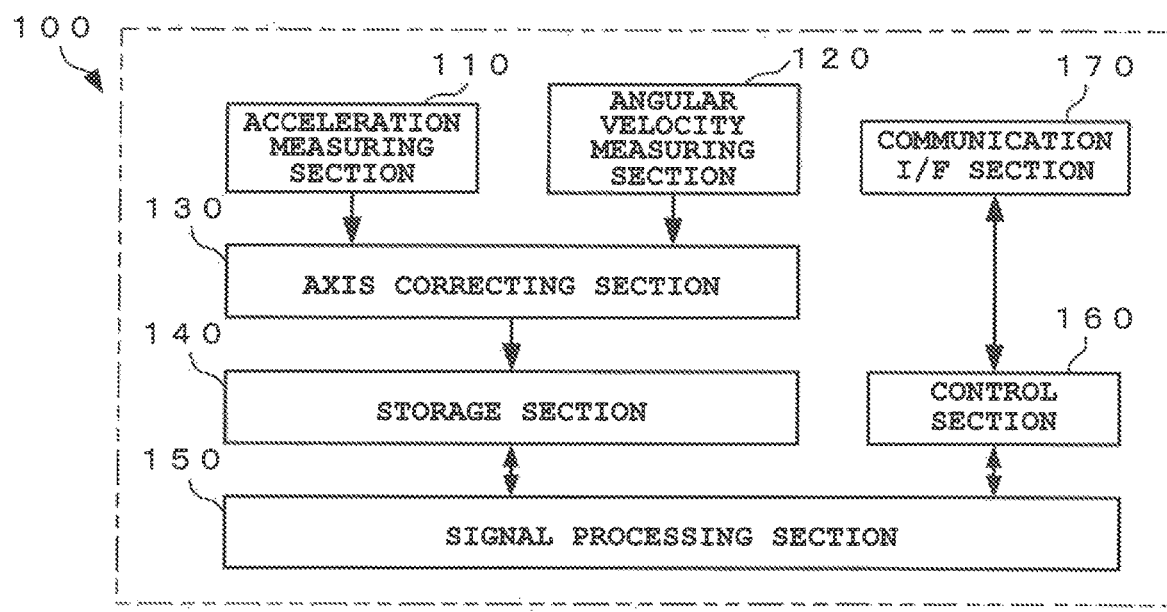
FIG. 2A and FIG. 2B are functional block diagrams showing respective sections applied in the exercise support device according to the first embodiment.
Figure 2B:
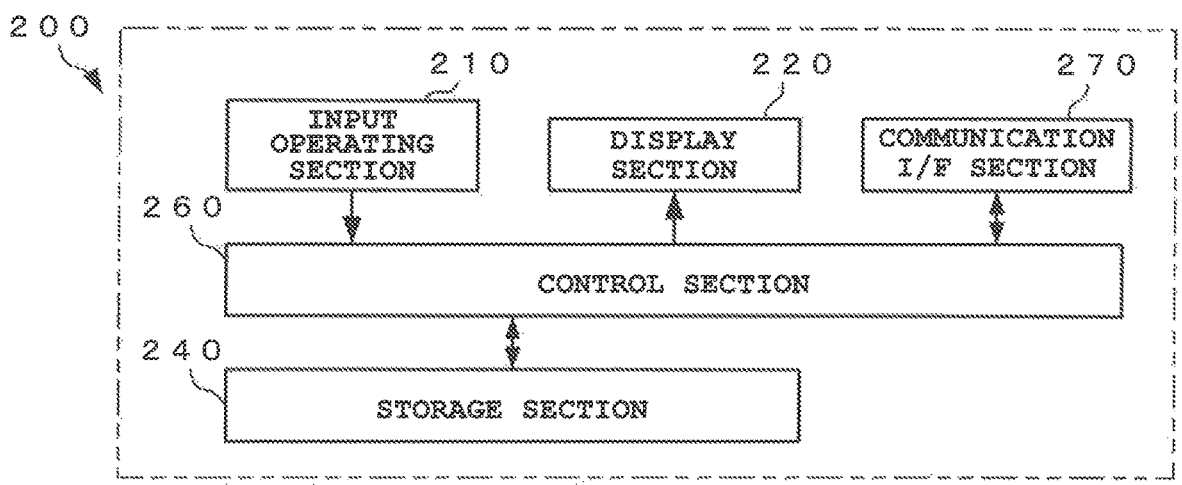
Figure 3:
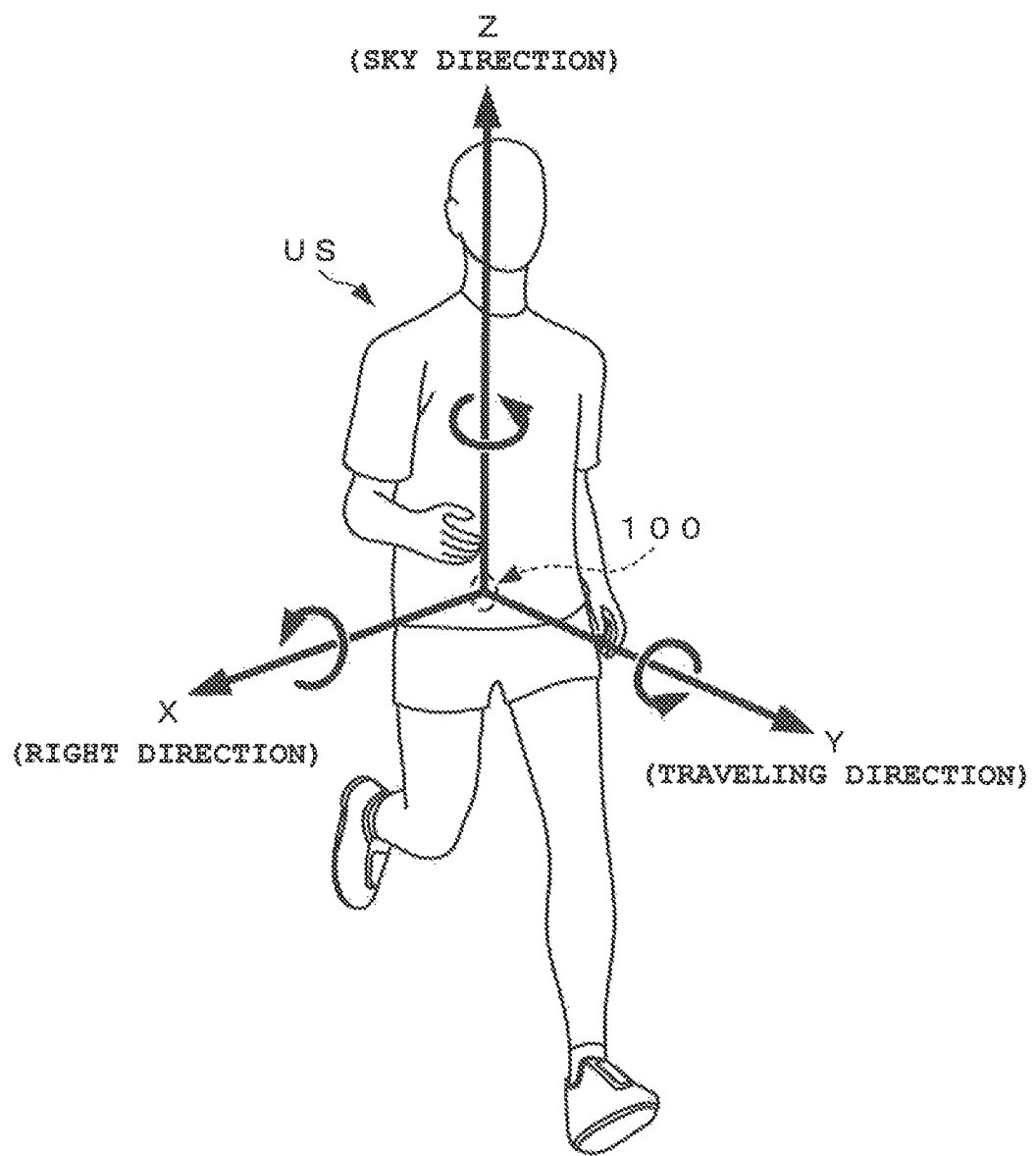
FIG. 3 is a schematic diagram of three axis directions in an acceleration sensor and an angular velocity sensor applied in the first embodiment.

FIG. 1 is a schematic view of an exercise support device according to a first embodiment of the present invention. FIG. 2A and FIG. 2B are functional block diagrams showing respective sections applied in the exercise support device according to the first embodiment, of which FIG. 2A is a functional block diagram showing the structure of a sensor device, and FIG. 2B is a functional block diagram showing the structure of a wrist device. FIG. 3 is a schematic diagram of three axis directions in a motion sensor applied in the present embodiment.

The exercise support device according to the first embodiment, for example, has a sensor device 100 that is worn on a portion of the waist of a user US on the back side and a wristwatch-type or wristband-type control device (hereinafter referred to as "wrist device" for convenience of explanation) 200 that is worn on a wrist or the like of the user US, as depicted in FIG. 1, so that the sensor device 100 travels with the user US when the user US travels.

The sensor device 100 has a function for measuring the body motion of a person performing an exercise involving movements such as a running exercise or a marathon by using a motion sensor (acceleration measuring section and angular velocity measuring section) and, based on collected sensor data, calculating various data regarding the exercise status of the user US including an exercise index indicating a left/right balance in the use of the body in the exercise. In FIG. 1, the sensor device 100 is worn on the waist of the user US. However, the present invention is not limited thereto, and the sensor device 100 may be worn on another part such as the chest, neck, or abdomen as long as it is worn on the body axis passing through the center of the body or a portion nearby. Also, a method of wearing the sensor device 100 on the body is not particularly limited, and various wearing methods can be adopted as appropriate, such as a method where the sensor device 100 is clipped to training clothes, a method where the sensor device 100 is attached by a tape member or the like, and a method where the sensor device 100 is wound around a body with a belt or the like.

Specifically, the sensor device 100 includes an acceleration measuring section 110, an angular velocity measuring section 120, an axis correcting section 130, a storage section 140, a signal processing section 150, a control section 160, a communication interface section (hereinafter abbreviated as "communication I/F section") 170, and the like, as depicted in FIG. 2A.

The acceleration measuring section (sensor section) 110 measures the ratio of change in motion speed during the user's exercise. This acceleration measuring section 110, which has a triaxial acceleration sensor, detects acceleration (acceleration signal) along each of three axes orthogonal to one another and outputs it as acceleration data. In the present embodiment, the sensor device 100 (acceleration measuring section 110) is worn on the waist of the user US such that a travelling direction is set as a +Y-axis direction, a right direction is set as +X-axis direction, and a sky direction orthogonal to an X-Y plane is set as +Z-axis direction with respect to the user US during a running exercise, as depicted in FIG. 3. The acceleration data (acceleration data AccX, AccY, and AccZ on the respective X, Y, and Z axes) acquired by the acceleration measuring section 110 is associated with time data representing elapsed time, and stored in the storage section 140 described further below.

The angular velocity measuring section (sensor section) 120 measures change in a motion direction (angular velocity) during the user's exercise. This angular velocity measuring section 120 has a triaxial angular velocity sensor and detects, for each of three axes orthogonal to one another and defining the above-described acceleration data, an angular velocity (angular velocity signal) occurring in the rotating direction of a rotating motion centering on each axis for output as angular velocity data. In the present embodiment, for the three axes of X, Y, and Z orthogonal to one another, the direction of an angular velocity occurring in a clockwise direction toward the +direction of acceleration on each axis is defined as a +direction, as depicted in FIG. 3. Angular velocity data (angular velocity data GyrX, GyrY, and GyrZ on the respective X, Y, and Z axes) acquired by the angular velocity measuring section 120 is associated with time data representing elapsed time, and stored in the storage section 140.

The axis correcting section 130 performs axis correction processing on the sensor data (acceleration data and angular velocity data) acquired by the acceleration measuring section 110 and the angular velocity measuring section 120. Specifically, since the waist of the body on the back side is generally tilted forward with respect to the vertical axis indicating the gravity direction vertical to the ground even in an upright state, the axis in the up-and-down direction (Z-axis) of the attached sensor device 100 is also tilted forward with respect to the vertical axis. When the user US starts running, the waist is further tilted and the Z-axis of the sensor device 100 is more tilted. Therefore, angular fluctuations due to the running motion are further added to the acquired sensor data. Here, the axis correcting section 130 first averages accelerations on each axis for several cycles of the running motion. By this averaging, acceleration components in the gravity direction remain (are extracted). Therefore, based on these extracted components, a gravity direction is specified. The axis correcting section 130 corrects the acceleration data and the angular velocity data by rotating each axis of the acceleration signal and the angular velocity signal such that the ceiling (upper) direction of the acceleration data acquired by the acceleration measuring section 110 coincides with the specified gravity direction described above.

The storage section 140 has at least one of a flash ROM (Read-Only Memory) and a RAM (Random Access Memory) and memorizes instructions which, when executed by the signal processing section 150 and/or the control section 160, control the signal processing section 150 and/or the control section 160. The storage section 140 stores, in a predetermined storage area, the sensor data (acceleration data and angular velocity data) axially-corrected by the axis correcting section 130 in association with time data representing elapsed time. Also, by the signal processing section 150 and the control section 160 executing a predetermined control program and/or algorithm program, the storage section 140 stores, in a predetermined storage area, various data regarding the exercise status including an exercise index calculated based on the sensor data. Note that the storage section 140 may be partially or entirely in a form of a removable storage medium, and may be structured to be removable from the sensor device 100.

The signal processing section (footstep judgment processing section, left/right landing judgment section, and measurement control section) 150 is an arithmetic processing device such as a CPU (Central Processing Unit) or MPU (Microprocessor) and executes various processes according to the instructions stored in the storage section 140. The signal processing section 150 judges, in response to an instruction from the control section 160, that executes various processes according to at least one user operation and/or the instructions stored in the storage section 140, whether a landed foot is the left foot or the right foot based on the sensor data after the axis correction stored in the storage section 140, and calculates various data regarding the exercise status of the user US including an exercise index indicating a left/right balance in the use of the body during exercise.

The control section (measurement control section) 160 is an arithmetic processing device such as a CPU or a MPU having a clock function and, based on a predetermined operating clock, executes a predetermined control program. In one embodiment, the CPU or the MPU functions as the signal processing section 150 may function as the control section 160, as well. In instead embodiments, the sensor device 100 of the exercise support device may comprise two or more of the CPU or the MPU function as the signal processing section 150 and the control section 160. As a result, the control section 160 controls sensing operations in the acceleration measuring section 110 and the angular velocity measuring section 120, an operation of storing and reading various data and the like in the storage section 140, an operation for communication with the wrist device 200 in the communication I/F section 170 described later, and the like. Also, by executing a predetermined algorithm program, the control section 160 controls axis correction processing on the sensor data in the axis correcting section 130, predetermined signal processing in the signal processing section 150 such as judgment as to whether a landed foot is the left foot or the right foot and the calculation of an exercise index and the like. Note that the signal processing to be executed in the signal processing section 150 and the control section 160 will be described later in detail.

The communication I/F section 170 communicates with at least the wrist device 200, receives a control signal from the wrist device 200, and thereby controls the start or end of each sensing operation in the acceleration measuring section 110 and the angular velocity measuring section 120. Also, the communication I/F section 170 transmits to the wrist device 200 the sensor data collected by the acceleration measuring section 110 and the angular velocity measuring section 120, various data regarding the exercise status calculated by the signal processing section 150 based on the sensor data, and the like. Here, as a method for transmitting and receiving various signals and data to and from the sensor device 100 and the wrist device 200 in the communication I/F section 170, various types of wireless communication methods such as Bluetooth (registered trademark) and Wi-Fi (Wireless Fidelity (registered trademark)) can be adopted.

Note that, in addition to the above-described acceleration measuring section 110 and the angular velocity measuring section 120, the sensor device 100 may include another measuring means, such as a measuring section including a geomagnetic sensor or a GPS (Global Positioning System) measuring section. Sensor data (such as geomagnetic data and positioning data) acquired by these measuring sections are stored in the storage section 140 in association with time data representing elapsed time. The sensor data can be used when, for example, various data regarding the exercise status calculated by the signal processing section 150 described above are analyzed in association with topographic and geographic conditions.

The wrist device 200 is worn on a portion (for example, wrist) of a human body where the wrist device 200 can be visually recognized by the user US easily, and is connected to the sensor device 100 by using a predetermined wireless communication method. This wrist device 200 has a function for giving an instruction to start or end a sensing operation in the sensor device 100 and a function for displaying various data regarding an exercise status calculated based on sensor data acquired by the sensor device 100 and the like. Here, in FIG. 1, the control device has a form of a wristwatch type (or wristband type) so as to be worn on a wrist of the user US. However, the present invention is not limited thereto. The control device may be, for example, a portable information terminal such as a smartphone or a dedicated terminal that can be accommodated in a pocket or worn on an upper arm.

Specifically, the wrist device 200 includes an input operating section 210, a display section 220, a storage section 240, a control section 260, a communication I/F section 270, and the like.

The input operating section 210 is input means, such as a button switch provided on the housing of the wrist device 200 and a touch panel provided on the front surface of the display section 220 described later. This input operating section 210 is used for an input operation when, for example, an instruction to start or end a sensing operation in the sensor device 100 is given or when desired information and the like are displayed on the display section 220 and various settings are performed, as depicted in FIG. 2.

The display section 220 has a display panel of, for example, a liquid-crystal type or light-emitting-element type, and displays at least information regarding an input operation by the input operating section 210, various data regarding the exercise status of the user US transmitted from the sensor device 100, and the like in a predetermined format. Note that, in addition to the above-described information, the display section 220 may display information regarding the operation status of the sensor device 100, time information, and the like.

The storage section 240 stores, in a predetermined storage area, at least various data regarding the exercise status of the user US transmitted from the sensor device 100 via the communication I/F section 270 described later. By executing a predetermined control program, the control section 260 controls an operation of displaying various data and the like in the display section 220, a data storing operation and a data reading operation in the storage section 240, a communication operation of the communication I/F section 270 with the sensor device 100, and the like.

By performing communication with the sensor device 100 by applying a predetermined wireless communication method, the communication I/F section 270 transmits to the sensor device 100 a control signal for indicating the start or end of a sensing operation in the sensor device 100 set by operating the input operating section 210 and the like. Also, the communication I/F section 270 receives various data regarding the exercise status of the user US calculated by the sensor device 100 and the like.

(Exercise Support Method)

Next, a control method (exercise support method) in the exercise support device according to the present embodiment is described with reference to the drawings. Note that the exercise support method described below is achieved by executing a predetermined algorithm program in the control section of each of the sensor device 100 and the wrist device 200.

Figure 4:
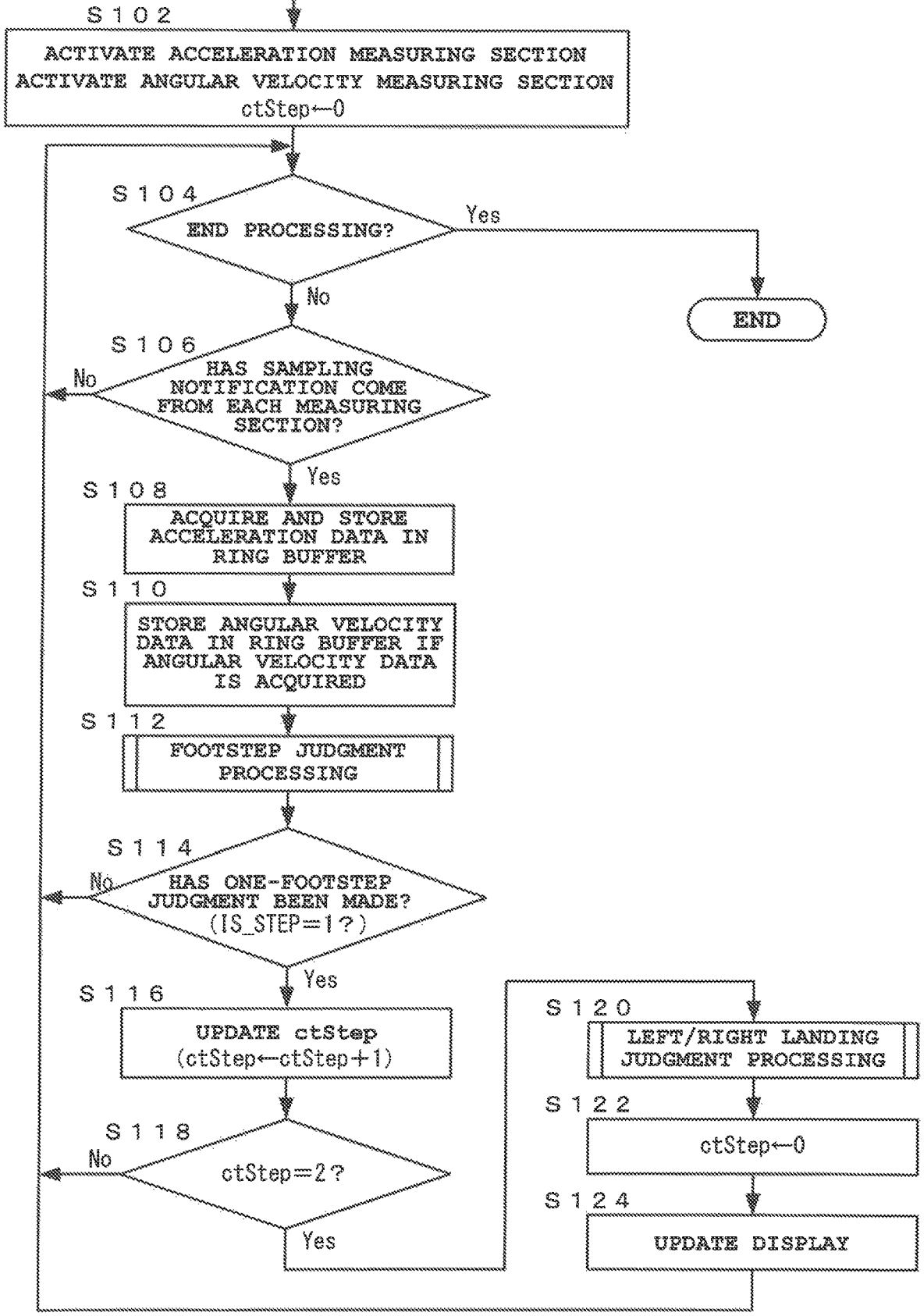
FIG. 4 is a flowchart of one example of an exercise support method according to the first embodiment.
Figure 5:
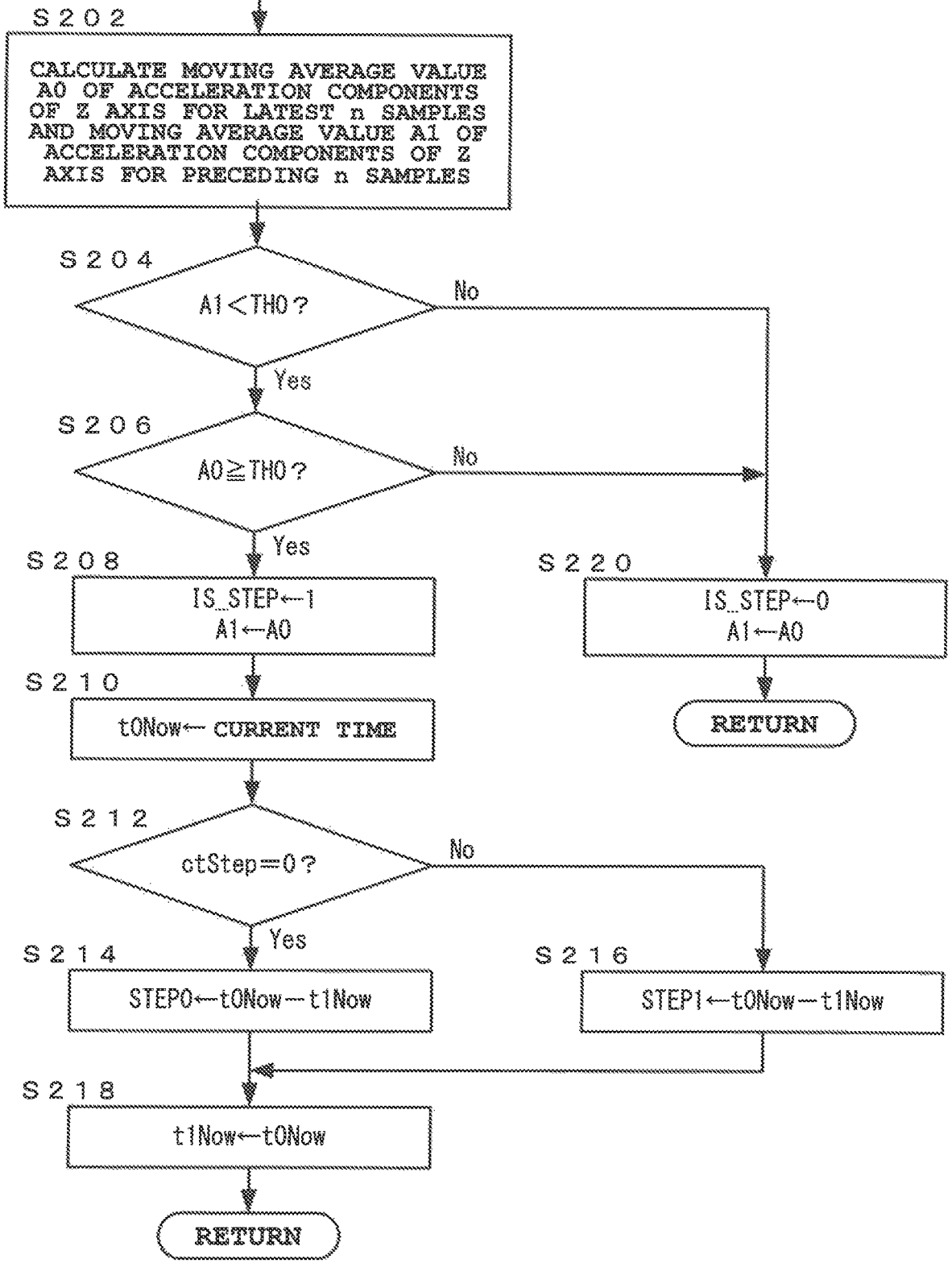
FIG. 5 is a flowchart of one example of footstep judgment processing applied in the exercise support method according to the first embodiment.
Figure 6:
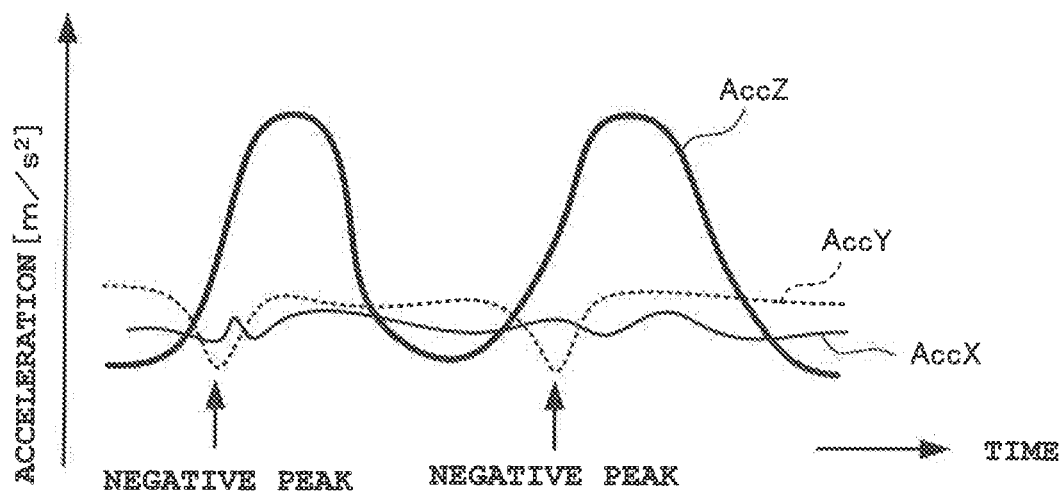
FIG. 6 is a waveform diagram of one example of acceleration waveforms (after smoothing filter processing) on respective axes acquired by an acceleration measuring section according to the first embodiment.
Figure 7:
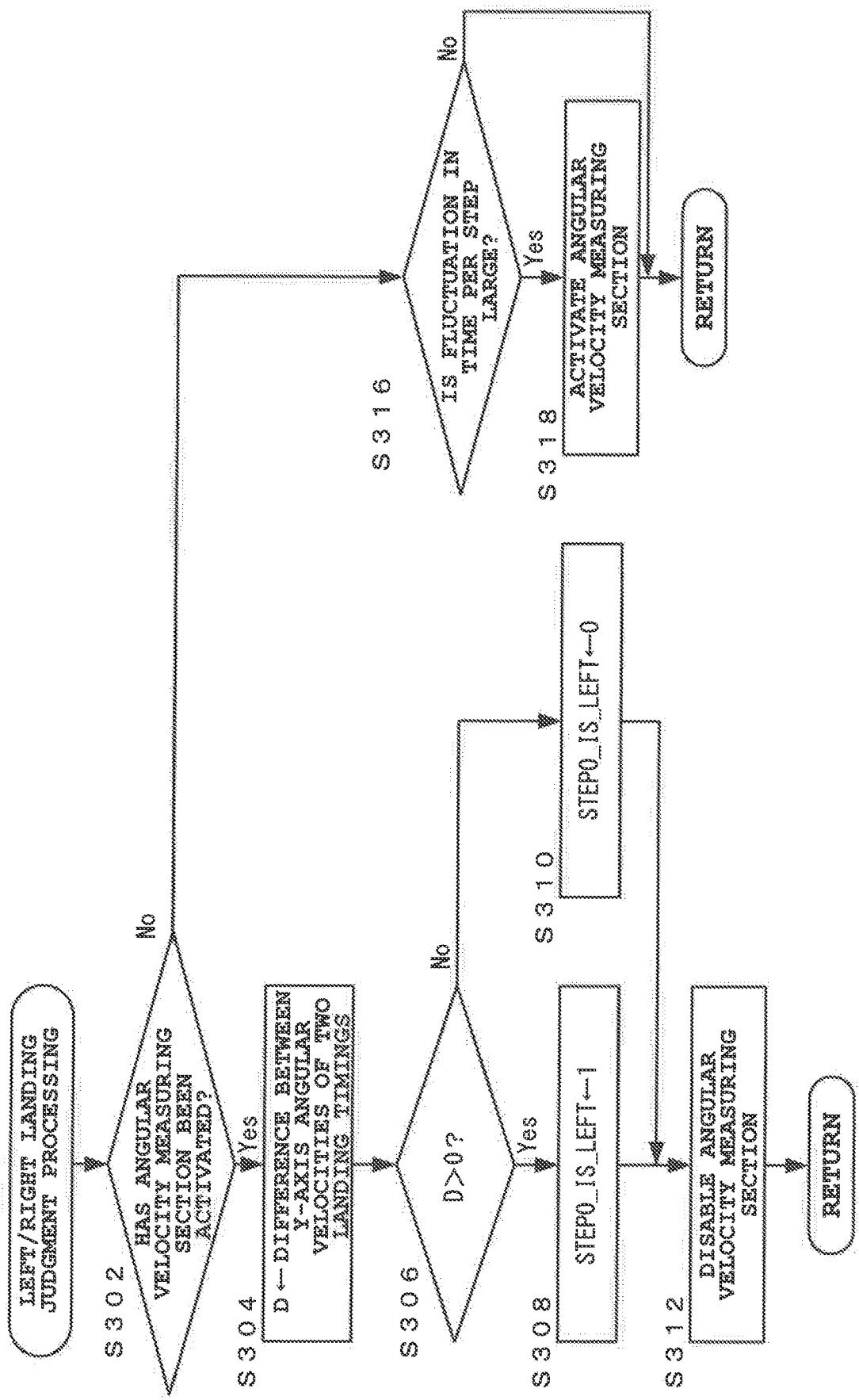
FIG. 7 is a flowchart of one example of left/right landing judgment processing applied in the exercise support method according to the first embodiment.
Figure 8:
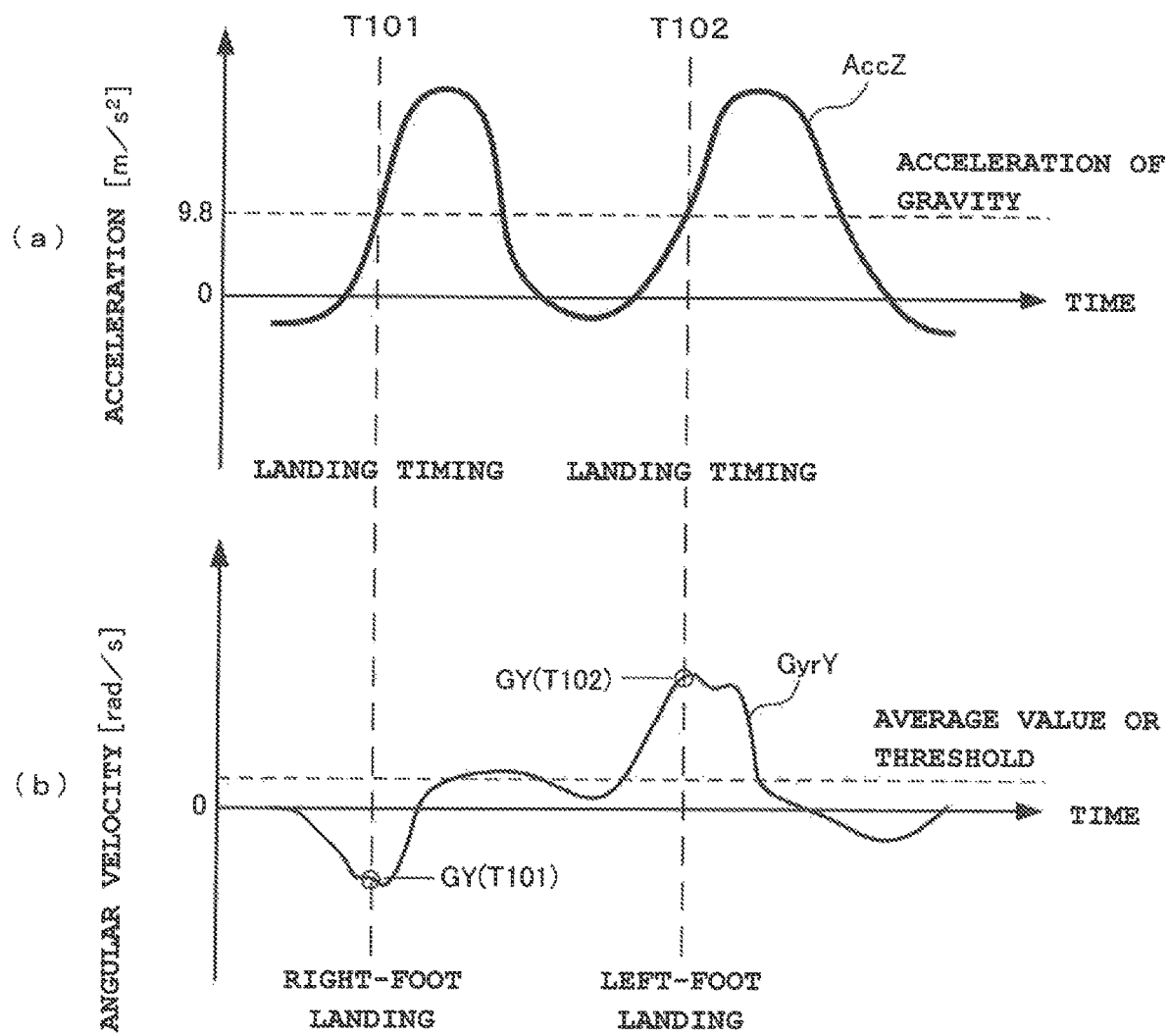
FIG. 8 is a waveform diagram of one example of an acceleration waveform (after smoothing filter processing) on a Z-axis acquired by the acceleration measuring section and an acceleration waveform acquired by an angular velocity measuring section according to the first embodiment.
Figure 9:
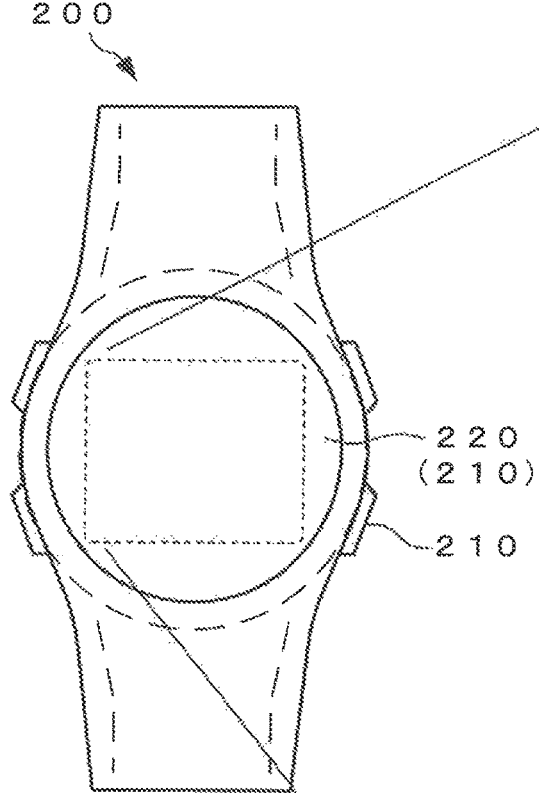
FIG. 9 is a diagram showing a display example of exercise indexes applied in the exercise support method according to the first embodiment.

FIG. 4 is a flowchart of one example of the exercise support method according to the present embodiment, and FIG. 5 is a flowchart of one example of footstep judgment processing applied in the exercise support method according to the present embodiment. FIG. 6 is a waveform diagram of one example of acceleration waveforms (after smoothing filter processing) on respective axes acquired by the acceleration measuring section according to the present embodiment, and FIG. 7 is a flowchart of one example of left/right landing judgment processing applied in the exercise support method according to the present embodiment. FIG. 8 is a waveform diagram of one example of an acceleration waveform (after smoothing filter processing) on a Z-axis acquired by the acceleration measuring section and an acceleration waveform acquired by the angular velocity measuring section according to the present embodiment, and FIG. 9 is a diagram showing a display example of exercise indexes applied in the exercise support method according to the present embodiment.

In the exercise support method according to the present embodiment, when starting a running exercise, the user US operates the wrist device 200 worn on a wrist or the like with the sensor device 100 being worn on the waist, and thereby starts a sensing operation by the sensor device 100, as depicted in the flowchart of FIG. 4. Specifically, by the user US operating the wrist device 200, a control signal indicating the start of a sensing operation in the sensor device 100 is transmitted from the wrist device 200 to the sensor device 100 via the communication I/F section 170. As a result, the control section 160 of the sensor device 100 performs an initial operation of activating the acceleration measuring section 110 and the angular velocity measuring section 120 and setting the value of a footstep counter ctStep for judging feet movements (two steps constituted by one step of the left foot and one step of the right foot) during the running exercise at "0" (Step S102). When activated by the control section 160, the acceleration measuring section 110 and the angular velocity measuring section 120 start sampling operations of acquiring sensor data based on a predetermined sampling frequency. Here, the sampling operations in the acceleration measuring section 110 and the angular velocity measuring section 120 are performed in synchronization with each other, and acceleration data and angular velocity data are acquired at the same timing.

Then, the control section 160 repeatedly performs a series of processing operations (Steps S106 to S124) described later until a control signal indicating the end of the sensing operation in the sensor device 100 is given by the operation of the wrist device 200 by the user US and received via the communication I/F section 170 and a processing end judgment is made (Step S104).

That is, the control section 160 first judges whether a notification regarding the acquisition (sampling) of sensor data has been given by each of the acceleration measuring section 110 and the angular velocity measuring section 120 (Step S106). Then, when a sampling notification is received from each of the acceleration measuring section 110 and the angular velocity measuring section 120 (Yes at Step S106), the control section 160 stores acceleration data acquired by the acceleration measuring section 110 in a ring buffer (Step S108). Conversely, when no sampling notification has been received, the control section 160 returns to Step S104 to continue the processing, and waits for a next sampling notification. Also, when the angular velocity measuring section 120 has been activated, the control section 160 stores angular velocity data in the ring buffer simultaneously with the above-described acquisition of the acceleration data (Step S110). Here, the ring buffer where the acceleration data and the angular velocity data are stored may be provided to the storage section 140 or the signal processing section 150 for performing footstep judgment processing described later.

Next, the control section 160 controls the signal processing section 150 to perform footstep judgment processing for judging each step of the left and right feet during the running exercise based on the acquired acceleration data (Step S112). In the footstep judgment processing according to the present embodiment, among the acceleration data acquired by the acceleration measuring section 110, Z-axis acceleration data AccZ (second component) is used to judge a foot movement for each footstep during the running exercise. That is, after being subjected to axis correction and smoothing filter processing, the acceleration data acquired by the acceleration measuring section 110 during the running exercise has characteristic waveforms on the respective X, Y, and Z axes, for example, as depicted in FIG. 6. Here, the cycle of the waveform in the Z-axis acceleration data AccZ, of which the acceleration value is significantly changed with time, corresponds to a footstep cycle representing each footstep. Accordingly, each footstep during the running exercise can be judged based on the Z-axis acceleration data AccZ.

In the footstep judgment processing, the signal processing section 150 first uses the Z-axis acceleration data AccZ of the latest (immediately-preceding) four samples among the acceleration data acquired by the acceleration measuring section 110 to calculate a moving average value A0 (Step S202), as depicted in the flowchart of FIG. 5.

Next, the signal processing section 150 judges whether the user's steps have advanced based on the moving average value A0 of the Z-axis acceleration data AccZ. Specifically, the signal processing section 150 judges whether the calculated moving average value A0 of the Z-axis acceleration data AccZ is larger than a moving average value A1 of Z-axis acceleration data AccZ calculated based on acceleration data acquired from the preceding sample and is equal to or larger than a previously set threshold TH0, and thereby detects a break between footsteps. That is, the signal processing section 150 judges whether the moving average value A1 is smaller than the threshold TH0 (Step S204) and, when the moving average value A1 is smaller than the threshold TH0 (Yes at Step S204), judges whether the moving average value A0 is equal to or larger than the threshold TH0 (Step S206). When the moving average value A1 is equal to or larger than the threshold TH0 (Yes at Step S206), the signal processing section 150 sets the moving average value A0 as the moving average value A1, judges that a break between footsteps has been detected and the user's steps have advanced, and sets a flag IS_STEP at 1. Subsequently, the signal processing section 150 stores the moving average value A1 and the flag IS_STEP in a predetermined storage area of the storage section 140 (Step S208). Here, for example, the threshold value TH0 for defining the magnitude of the calculated moving average value A0 of the Z-axis acceleration data AccZ may be set based on acceleration data acquired in a previous running exercise. For example, it is set on the order of 12 m/s$^2$.

On the other hand, when the moving average value A1 is equal to or larger than the threshold TH0 (No at Step S204) or when the moving average value A1 is smaller than the threshold TH0 and the moving average value A0 is smaller than the threshold TH0 (No at Step S206), the signal processing section 150 sets the moving average value A0 as the moving average value A1, judges that a break between footsteps has not been detected and the user's steps have not advanced, and sets the flag IS_STEP at 0. Subsequently, the signal processing section 150 stores the moving average value A1 and the flag IS_STEP in the predetermined storage area of the storage section 140 (Step S220), ends the footstep judgment processing, and returns to the flowchart depicted in FIG. 4. Note that the moving average value A1 calculated based on the acceleration data acquired from the preceding sample and applied to the above-described processing for judging whether the user's steps have advanced is indefinite in an initial state. Accordingly, in the case of a moving average value A0 calculated based on acceleration data acquired with first several samples, the signal processing section 150 does not perform the above-described judgment processing, judges that the user's steps have not advanced, sets the flag IS_STEP at 0, ends the footstep judgment processing, and returns to the flowchart depicted in FIG. 4.

Next, when judged that a break between footsteps has been detected and the user's steps have advanced in the above-described processing for judging whether the user's steps have advanced (Steps S204 and S206), the signal processing section 150 sets a parameter t0Now defining the time of a break between footsteps at a current time, and stores the parameter in a predetermined storage area of the storage section 140 (Step S210).

Next, based on the result of the above-described judgment processing regarding footsteps, the signal processing section 150 judges whether the user's steps have advanced by two steps. Specifically, the signal processing section 150 judges whether the value of the footstep counter ctStep for making a judgment regarding two footsteps is 0 (Step 3212). When the value of the footstep counter ctStep is 0 (Yes at Step S212), the signal processing section 150 judges that the user's steps have advanced by one step, sets a differential time between a parameter t1Now defining the time of the preceding break in the user's steps and the parameter t0Now set at the current time to a parameter STEP0, and stores the set parameter in a predetermined storage area of the storage section 140 (Step S214).

On the other hand, when the value of the footstep counter ctStep is not 0 (No at Step S212), the signal processing section 150 judges that the user's steps have advanced by more than two steps, and sets an elapsed time from the time set in the parameter t1Now defining the time of the preceding break in the user's steps to a parameter STEP1, and stores the set parameter in the predetermined storage area of the storage section 140 (Step S216). Here, the elapsed time set to the parameter STEP1 corresponds to a differential time between the parameter t1Now and the parameter t0Now.

Next, the signal processing section 150 sets the time of the parameter t0Now to the parameter t1Now, stores the set parameter in the predetermined storage area of the storage section 140 (Step S218), ends the footstep judgment processing, and returns to the flowchart depicted in FIG. 4. Note that the parameter t1Now defining the time of the preceding break in the user's steps applied to the above-described processing for calculating a time per step (Step S212 to S216) is indefinite in an initial state. Accordingly, in the case of the parameter t0Now defining the time of a break between footsteps based on acceleration data acquired from an initial sample, the signal processing section 150 does not perform the above-described calculation processing, performs only the processing for setting (updating) the parameter t1Now as the current time, sets the flag IS_STEP at 0, ends the footstep judgment processing, and returns to the flowchart depicted in FIG. 4.

Next, in the above-described footstep judgment processing (Step S112), the control section 160 judges whether the user's steps have advanced. Specifically, in the footstep judgment processing, the signal processing section 150 judges whether the flag IS_STEP indicating a result of judgment as to whether the user's steps have advanced has been set at 1 and the user's steps have advanced by one step (Step S114). When judged that the user's steps have advanced by one step (Yes at Step S114), the signal processing section 150 increments and updates the value of the footstep counter ctStep (ctStep←ctStep+1) (Step S116). Next, the signal processing section 150 judges whether the user's steps have advanced by two steps. Specifically, the signal processing section 150 judges whether the updated value of the footstep counter ctStep is 2 (Step S118). When the value of the footstep counter ctStep is 2 (Yes at Step S118), the signal processing section 150 judges that the user's steps have advanced by two steps, and performs left/right landing judgment processing for judging the landing of the left and right feet (Step S120).

On the other hand, in the footstep judgment processing, when the flag IS_STEP has not been set at 1 and the user's steps have not advanced by one step (No at Step S114) or when the value of the footstep counter ctStep is not 2 and the user's steps have not advanced by two steps (No at Step S118), the control section 160 returns to Step S104 to continue the processing, and waits until the next sampling notification is received.

In the left/right landing judgment processing (Step S120) according to the present embodiment, the control section 160 controls the signal processing section 150 to first judge whether the angular velocity measuring section 120 has been activated (Step S302), as depicted in the flowchart of FIG. 7. Here, the state in which the angular velocity measuring section 120 has been activated means that the angular velocity measuring section 120 has been supplied with drive power (power supply ON) and is operating effectively, and the state in which the angular velocity measuring section 120 has not been activated means that drive power to the angular velocity measuring section 120 has been interrupted (power supply OFF) or restricted and the angular velocity measuring section 120 is not effectively operating. When the angular velocity measuring section 120 has not been activated (has been disabled) (No at Step S302), the signal processing section 150 judges whether the fluctuation in time per step calculated in the above-described footstep judgment processing (Step S112) is large (Step S316). Here, in the judgment of the fluctuation in time per step, the fluctuation in time may be regarded as large if, for example, a difference between a time required for the first footstep set to the parameter STEP0 and a time required for the second footstep set to the parameter STEP1 is larger than a preset threshold. Alternatively, a configuration may be adopted in which an elapsed time for the latest ten footsteps is stored, their average value and a time required for the first footstep (set value of the parameter STEP0) or a time required for the second footstep (set value of the parameter STEP1) are compared and, if a difference therebetween is larger than a preset threshold, the fluctuation in time is regarded as large. Then, when the fluctuation in time per step is large (Yes at Step S316), the signal processing section 150 activates the angular velocity measuring section 120 (Step S318), ends the left/right landing judgment processing, and returns to the flowchart depicted in FIG. 4. On the other hand, when the fluctuation in time per step is small (No at Step S316), the signal processing section 150 ends the left/right landing judgment processing in this state, and returns to the flowchart depicted in FIG. 4. In this case, the value of a variable STEP0_IS_LEFT that has already been set is retained.

At Step S302, when the angular velocity measuring section 120 has been activated (Yes at Step S302), the signal processing section 150 judges the landing of the left and right feet during the running exercise by using Y-axis angular velocity data (first component) GyrY among the angular velocity data on the respective axes acquired by the angular velocity measuring section 120. Specifically, the waveform of the Z-axis acceleration data AccZ after smoothing filter processing among the acceleration data acquired by the acceleration measuring section 110 during the running exercise is represented as, for example, diagram (a) of FIG. 8. Also, the waveform of the Y-axis angular velocity data GyrY in the angular velocity data acquired by the angular velocity measuring section 120 is represented as, for example, diagram (b) of FIG. 8. In diagrams (a) and (b) of FIG. 8, time axes coincide with each other. Here, the Y-axis angular velocity data GyrY in the angular velocity data indicates a tendency of generally reverse changes in accordance with the left and right footsteps. When the left foot is landed, the Y-axis angular velocity data GyrY indicates a positive (plus) value. When the right foot is landed, the Y-axis angular velocity data GyrY indicates a negative (minus) value. This change tendency of the Y-axis angular velocity data GyrY tends to significantly appear after a slight delay from the landing timing of each of the left and right feet. Also, the landing timing of the left or right foot is present slightly before time points T101 and T102 at which the value of the Z-axis acceleration data AccZ after smoothing filter processing in the acceleration data is increased to exceed the acceleration of gravity (9.8 m/s$^2$). Therefore, the landing of the left and right feet can be judged based on the Y-axis angular velocity data GyrY in the angular velocity data at the time points T101 and T102 at which the Z-axis acceleration data AccZ in the acceleration data exceeds the acceleration of gravity (that is, immediately after the landing timing).

That is, the signal processing section 150 calculates a value (difference) by subtracting, from the value GY (T102) of the Y-axis angular velocity data GyrY in the angular velocity data at the immediately-preceding time point T102, the value GY (T101) of the Y-axis angular velocity data GyrY at the time point T101 immediately before T102, and sets the calculated value as parameter D (Step S304). Note that, in the waveforms depicted in diagrams (a) and (b) of FIG. 8, parameter D is set at a positive value. On the other hand, at the opposite-foot landing timing, parameter D is set at a negative value. Here, in the present embodiment, the unit of parameter D is [rad/s].

Next, the signal processing section 150 judges whether parameter D is a positive value (D>0) (Step S306). When parameter D is a positive value (Yes at Step S306), the signal processing section 150 judges that the foot landed immediately before the latest time point T102 is the left foot, sets the variable STEP0_IS_LEFT at 1, and stores the set value in a predetermined storage area of the storage section 140 (Step S308). On the other hand, when parameter D is a negative value (No at Step S306), the signal processing section 150 judges that the foot landed immediately before the latest time point T102 is the right foot, sets the variable STEP_IS_LEFT at 0, and stores the set value in the predetermined storage area of the storage section 140 (Step S310). Then, the signal processing section 150 disables the angular velocity measuring section 120 (Step S312), ends the left/right landing judgment processing, and returns to the flowchart depicted in FIG. 4.

Next, the control section 160 performs initialization to set the value of the footstep counter ctStep at "0" (Step S122). Then, the control section 160 transmits various data, judgment results, and the like acquired in the above-described footstep judgment processing (Step S112) and left/right landing judgment processing (Step 6120) to the wrist device 200 via the communication I/F section 170. As a result, various data regarding the steps of the left and right feet during the running exercise are displayed on the display section 220 of the wrist device 200 in substantially real time in a predetermined format such as numerical values, characters, icons, or the like as exercise indexes so as to be provided to the user US (Step S124).

Specifically, as the exercise indexes to be displayed on the display section 220 of the wrist device 200, a pitch (upper portion in FIG. 9) and elapsed times between landing timings of the respective left and right feet (intermediate and lower portions in FIG. 9) calculated based on various data and the judgment results acquired in the footstep judgment processing and the left/right landing judgment processing are displayed by use of numerical values, characters, or the like, as depicted in drawing (a) of FIG. 9. Here, since the pitch is a step count per minute (unit: [bpm]), it is calculated by the following equation based on the value set in the parameters STEP0 and STEP1 in the above-described footstep judgment processing. Note that, in drawing (a) of FIG. 9, "169 bpm" is shown as an example of calculation.

(pitch)=60/(STEP0+STEP1)

In addition, as the elapsed time from the landing timing of the right foot to the landing timing of the left foot, the value set to the parameter STEP1 (for example, "180 ms" is shown in drawing (a) of FIG. 9) is displayed on the display section 220 if the variable STEP0_IS_LEFT has been set at 1 in the above-described left/right landing judgment processing. Also, as the elapsed time from the landing timing of the left foot to the landing timing of the right foot, the value set to the parameter STEP0 (for example, "176 ms" is shown in drawing (a) of FIG. 9) is displayed on the display section 220 if the variable STEP0_IS_LEFT has been set at 1 in the above-described left/right landing judgment processing.

In drawing (a) of FIG. 9, the pitch and the elapsed times between the landing timings of the respective left and right feet are displayed as exercise indexes on the display section 220 of the wrist device 200. However, the present invention is not limited thereto. That is, in the present invention, various data regarding alternate movements of the left and right feet may be displayed as an exercise index as long as they are related to the steps of the left and right feet, and various data regarding independent movements of each of the left and right feet may be displayed as an exercise index. Here, as an example of the latter case, a value indicating up-and-down movements of the user's body during a running exercise acquired by integrating Z-axis acceleration data AccZ among pieces of acceleration data may be displayed as an exercise index. As a result, a fluctuation amount of the up-and-down movements of the body from the landing timing of the right foot to the landing timing of the left foot and a fluctuation amount of the up-and-down movements of the body from the landing timing of the left foot to the landing timing of the right foot can be grasped or can be compared with each other to be grasped.

Then, the control section 160 returns to Step S104 to repeatedly perform the above-described series of processing operations (Steps S106 to S124) until a processing end judgment is made.

As such, in the present embodiment, based on changes in vertical acceleration with respect to the ground (Z-axis acceleration data AccZ after axis correction) acquired during a running exercise, the landing timings of the left and right feet during the running exercise are detected and, based on whether a difference (parameter D) between angular velocities (Y-axis angular velocity data GyrY) around a traveling direction axis immediately after the latest landing timing and the preceding landing timing is a positive or negative value, it is judged whether the current landed foot is the left foot or the right foot.

As a result of this configuration, when the user runs with the sensor device being attached to the waist and even if the rotation of the waist portion is not appropriately detected because the attachment position of the sensor device is vertically shifted due to vibrations or the like, the exercise support device according to the present embodiment can correctly judge whether a landed foot is the right foot or the left foot based on angular velocities around a traveling direction axis, and thereby provides an exercise index to the user. Therefore, the user can accurately grasp a balance in the use of the body in the exercise for judgment and improvement.

Also, in the present embodiment, even if the attachment position of the sensor device is shifted to some extent due to vibrations or the like in a running exercise, whether a landed foot is the left foot or the right foot can be correctly judged. Therefore, as an attachment structure of the sensor device, a simple structure can be applied. For example, the sensor device may be fixed to running wear with a clip.

Moreover, in the exercise support method according to the present embodiment, once a left/right landing judgment is made, the angular velocity measuring section is disabled. Also, it is judged whether a change in acceleration in the vertical direction is cyclic and, if it is not cyclic, the angular velocity measuring section is activated, and the left/right landing judgment processing is restarted based on angular velocities around a traveling direction axis (Y-axis angular velocity data GyrY).

That is, in the present embodiment, for left/right foot landing judgment, an angular velocity measuring section whose power consumption is generally larger than an acceleration measuring section is used. For this reason, in the present embodiment, intermittent driving is performed in which, once a left/right landing judgment is made, the angular velocity measuring section is disabled and then again activated when left/right landing judgment processing is required. As a result of this configuration, the power consumption of the angular velocity measuring section can be minimized as much as possible, and low power consumption of the sensor device can be achieved. Here, when a change in acceleration in the vertical direction becomes non-cyclic, such as when the user stumbles or stops running, the angular velocity measuring section is activated to restart left/right landing judgment processing, and thereby appropriately makes a left/right landing judgment.

In the present embodiment, as a method for detecting the landing timings of the left and right feet during a running exercise, the method has been adopted in which Z-axis acceleration data AccZ is used among pieces of acceleration data acquired by the acceleration measuring section. However, the present invention is not limited thereto and, for example, Y-axis acceleration data AccY among the acceleration data may be used to detect the above-described landing timings. Specifically, in the case of the acceleration data on the respective X, Y, and Z axes in FIG. 6, the landing timings of the left and right feet can be detected by extracting the time points of negative peak values appearing in the Y-axis acceleration data AccY during a period in which the Z-axis acceleration data AccZ after smoothing filter processing tends to increase.

Also, in the present embodiment, as a method for judging whether a landed foot is the left foot or the right foot, the method has been adopted in which the polarity (positive or negative value) of a specific parameter regarding Y-axis acceleration data GyrY among angular velocity data acquired by the angular velocity measuring section is used. However, the present invention is not limited thereto. In the present invention, for example, a method using Y-axis angular velocity data GyrY, a method using X-axis acceleration data AccX, a method using Z-axis angular velocity data GyrZ may be used to judge whether a landed foot is the left foot or the right foot, as explained in a third embodiment described later. These methods will be described in detail further below.

Moreover, in the present embodiment, the left/right landing judgment processing is intermittently performed such that, once a left/right landing judgment is made, the angular velocity measuring section is disabled. However, the present invention is not limited thereto. For example, a configuration may be adopted in which the angular velocity measuring section is continuously enabled for a specific period to continuously perform the left/right landing judgment processing a plurality of times, the judgment results are filtered (evaluated, judged, and narrowed down) to be provided to the user as an exercise index, and the angular velocity measuring section is continuously disabled after the end of the specific period.

Modification Example

Next, a modification example of the above-described present embodiment is described with reference to the drawings.

Figure 10:
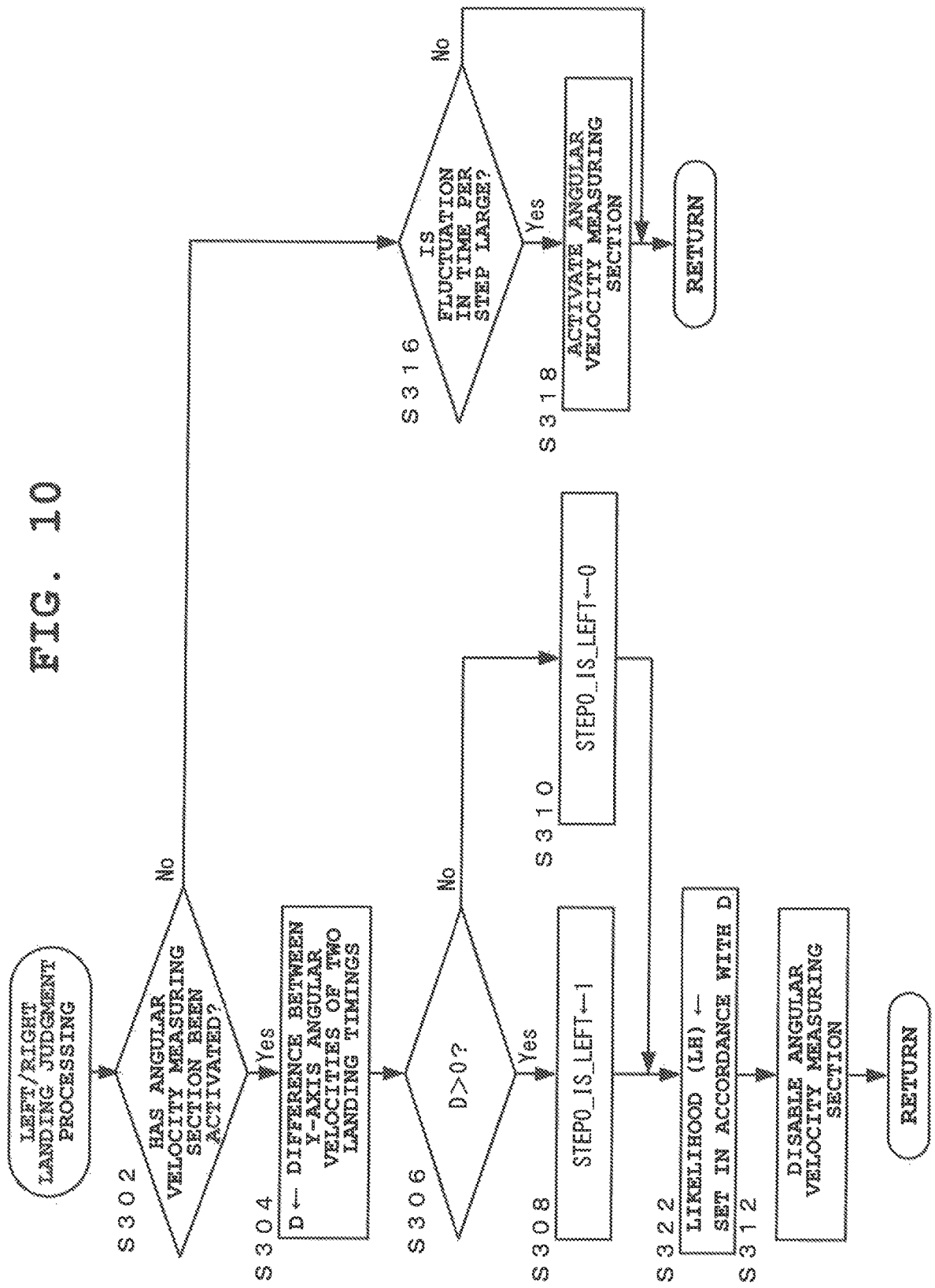
FIG. 10 is a flowchart of a modification example of the exercise support method according to the first embodiment.

FIG. 10 is a flowchart of the modification example of the exercise support method according to the above-described present embodiment. Note that processing operations equivalent to those in the above-described present embodiment are described in a simplified manner.

In the above-described present embodiment, based on various data and judgment results acquired in the footstep judgment processing and the left/right landing judgment processing, an exercise index regarding the steps of the left and right feet during a running exercise is displayed on the display section 220 of the wrist device 200. A modification example of this embodiment has a feature in which the method of displaying an exercise index on the display section 220 of the wrist device 200 is changed based on a likelihood indicating the stability or correctness of a result of the left/right landing judgment processing.

That is, in this modification example, in the left/right landing judgment processing (Step S120), the signal processing section 150 calculates a difference between the Y-axis angular velocity data GyrY acquired by the angular velocity measuring section 120 at the time points T101 and T102 when the Z-axis acceleration data AccZ exceeds the acceleration of gravity as depicted in drawings (a) and (b) of FIG. 8, and sets the difference as parameter D (Step S304), as with the above-described first embodiment. Then, based on whether parameter D has a positive or negative value, the signal processing section 150 judges whether the most recently landed foot is the left foot or the right foot (Steps S306 to S310).

Then, in the modification example of the present embodiment, the signal processing section 150 sets, based on the value of parameter D, a likelihood (plausibility) LH indicating the statistical stability and correctness of the results of the above-described left/right landing judgment processing (Step S322), as depicted in the flowchart of FIG. 10. Here, the likelihood LH indicates the stability and correctness of the left/right landing judgment in a range of values from 1 to 0. When the stability and correctness are high, a value of 1 is used. When the stability and correctness are low, a value closer to 0 is used. That is, when the value of parameter D is far from 0 that indicates a boundary between positive and negative values, the result of the left/right landing judgment processing has higher stability and correctness. As a result, for example, when the absolute value of parameter D is equal to or larger than 2 (that is, D≥+2 or D≥−2), the signal processing section 150 sets the likelihood LH at 1. On the other hand, when the absolute value of the parameter D is smaller than 2 (that is, −2<D<+2), the signal processing section 150 sets the likelihood LH as follows. Here, "s" is an adjustment factor and is set at, for example, 1, and "Abs(_)" is a function for acquiring an absolute value.

$$LH=\exp(-(2-\text{Abs}(D))/s)$$

Then, after storing the above-described likelihood LH in a predetermined storage area of the storage section 140, the signal processing section 150 disables the angular velocity measuring section 120 (Step S312), ends the left/right landing judgment processing, and returns to the flowchart depicted in FIG. 4, as in the case of the above-described embodiment.

Next, after initializing the footstep counter ctStep (Step S122), the control section 160 causes an exercise index based on various data, the judgment results, and the like acquired in the above-described footstep judgment processing and left/right landing judgment processing to be displayed on the display section 220 of the wrist device 200 in a predetermined format in substantially real time and provided to the user US (Step S124).

In the present modification example, examples of the exercise index to be displayed on the display section 220 of the wrist device 200 include a pitch (upper portion in FIG. 9), elapsed times between the landing timings of the respective left and right feet (intermediate and lower portions in FIG. 9), and the like based on various data, the judgment results, and the like acquired in the footstep judgment processing the left/right landing judgment processing, and they are displayed in a predetermined format according to the above-described likelihood LH, as depicted in drawing (b) of FIG. 9. Here, the display format of the exercise indexes to be displayed on the display section 220 is set such that the magnitude of the likelihood LH (that is, the stability and correctness of the results of the left/right landing judgment processing) can be intuitively and instantaneously recognized by the user viewing the display section 220. Specifically, the likelihood LH itself may be displayed on the display section 220 as numerical value information or, for example, the display density, display color, and the like of the exercise index regarding the left/right landing judgment may be changed in accordance with the likelihood LH, as depicted in drawing (b) of FIG. 9. Here, a low likelihood LH indicates low stability and correctness of the left/right landing judgment. Therefore, when the likelihood LH set in the above-described left/right landing judgment processing is low, display prompting the user to makes an improvement may be displayed to the user. Specifically, for example, at timing at which the left foot is landed during a running exercise, display may be made to prompt the user to tap the front surface of the touch panel or operate a button switch so as to set landing timing and making a left/right landing judgment by a manual operation, as depicted in drawing (c) of FIG. 9.

As such, in the present modification example, based on the difference (parameter D) of angular velocities around a traveling direction axis calculated in the left/right landing judgment processing, a likelihood indicating stability and correctness in the left/right landing judgment is set, and an exercise index is provided to the user in a display format in accordance with the likelihood. Here, when the likelihood is low, the likelihood is displayed in a format easily recognizable by the user. In addition, display is made to prompt the user to make an improvement and set landing timing by the user's manual operation, and a left/right landing judgment is made, so that the result of the left/right landing judgment processing in the sensor device is substantially disabled.

As a result of this configuration, in the present modification example, operations and effects equivalent to those in the above-described embodiment can be achieved. Also, the exercise index can be provided to the user in a display format in accordance with stability and correctness (likelihood) in the left/right landing judgment. Here, when stability and correctness in the left/right landing judgment are low, the user is prompted to perform a manual operation to set landing timing and cause a left/right landing judgment to be made. Therefore, the user can more appropriately grasp a balance in the use of the body at the time of exercise for judgment and improvement.

Second Embodiment

Next, an exercise support device according to a second embodiment of the present invention is described with reference to the drawings.

Figure 11:
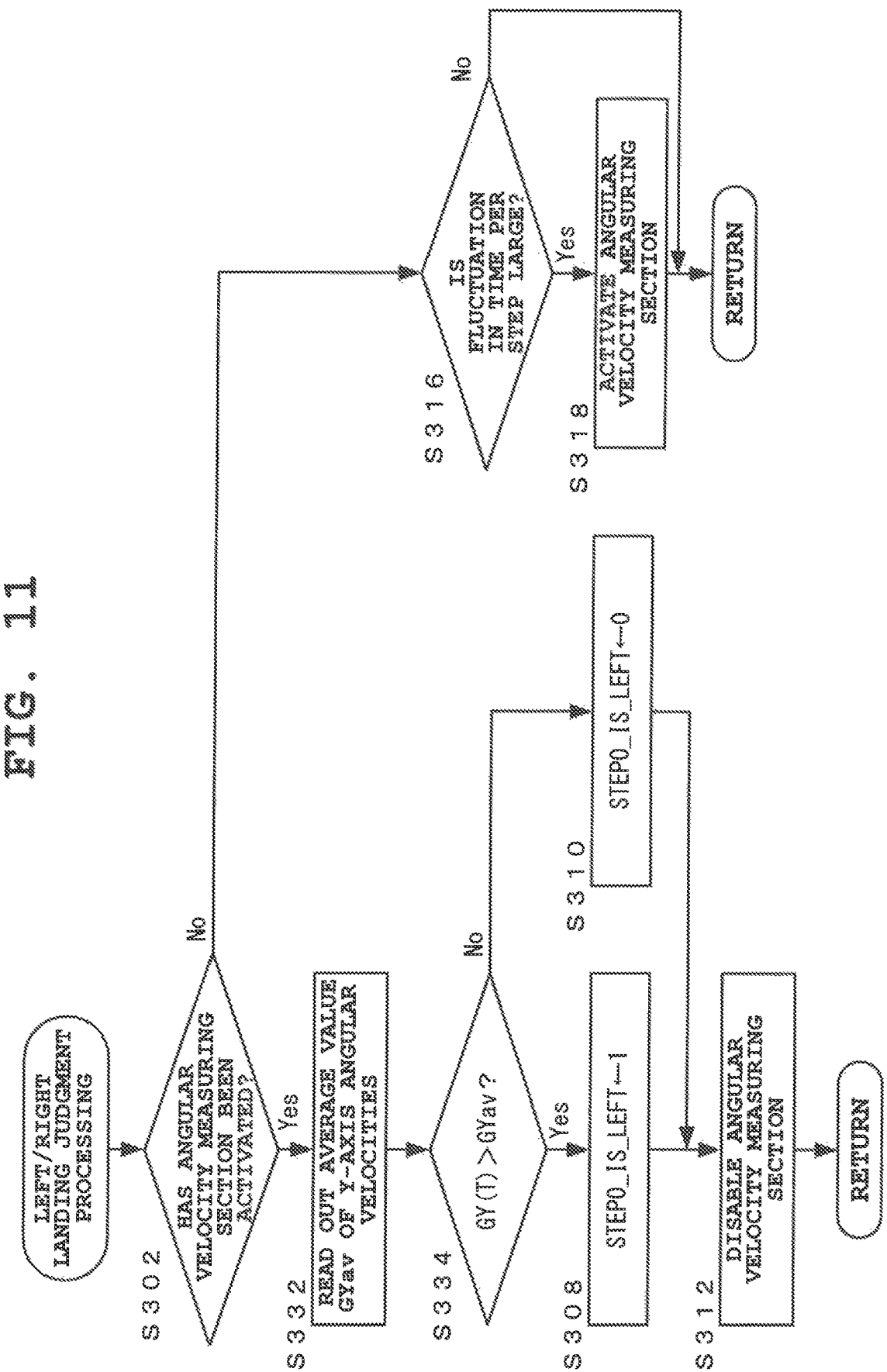
FIG. 11 is a flowchart of one example of left/right landing judgment processing applied in an exercise support method according to a second embodiment.

FIG. 11 is a flowchart of one example of left/right landing judgment processing applied in the exercise support method according to the second embodiment. Here, processing operations equivalent to those in the above-described first embodiment and modification example thereof are described in a simplified manner.

In the above-described first embodiment, whether a landed foot is the left foot or the right foot is judged based on whether a difference (parameter D) between angular velocities around a traveling direction axis (Y-axis angular velocity data GyrY) at latest timing and the preceding timing has a positive value or a negative value. The second embodiment has a feature in which whether a landed foot is the left foot or the right foot is judged based on the average value of angular velocities around a traveling direction axis (Y-axis angular velocity data GyrY) calculated in advance based on sensor data acquired in a specific period or a magnitude relation of an angular velocity around a traveling direction axis at latest landing timing with respect to a predetermined threshold set in advance.

That is, in the second embodiment, in the left/right landing judgment processing (Step S120) applied in the exercise support method (refer to the flowchart of FIG. 4) of the first embodiment, the control section 160 controls the signal processing section 150 to first judge whether the angular velocity measuring section 120 has been activated (Step S302), as depicted in the flowchart of FIG. 11. When judged that the angular velocity measuring section 120 has been activated (Yes at Step S302), the signal processing section 150 reads out the average value GYav of Y-axis angular velocity data GyrY stored in a predetermined storage area of the storage section 140 (Step S332), and judges whether the value GY(T) of Y-axis angular velocity data GyrY at the latest landing timing acquired by the angular velocity measuring section 120 is larger than the average value GYav (Step S334). Here, the average value GYav of the Y-axis angular velocity data GyrY is calculated by using Y-axis angular velocity data GyrY among sensor data acquired by the angular velocity measuring section 120 for a specific period (for example, sensor data for several to ten footsteps) in the latest or previous running exercise, and is stored in advance in the predetermined storage area of the storage section 140.

Then, when the value GY(T) of the Y-axis angular velocity data GyrY is larger than the average value GYav (Yes at Step S334), the signal processing section 150 judges that the foot landed at that timing is the left foot, and sets a variable STEP0_IS_LEFT at 1 (Step S308). On the other hand, when the value GY(T) of the Y-axis angular velocity data GyrY is equal to or smaller than the average value GYav (No at Step S334), the signal processing section 150 judges that the foot landed at that timing is the right foot, and sets a variable STEP0_IS_LEFT at 0 (Step S310). Then, the signal processing section 150 disables the angular velocity measuring section 120 (Step S312), ends the left/right landing judgment processing, and returns to the flowchart depicted in FIG. 4.

As such, in the present embodiment, a left/right landing judgment can be made based on a magnitude relation between an average value calculated in advance and Y-axis angular velocity data GyrY at latest landing timing. Therefore, a left/right landing judgment during a running exercise can be accurately made only with sensor data for one footstep serving as a judgment target. In the above-described first embodiment, since a left/right landing judgment is made based on a difference (parameter D) between Y-axis angular velocity data GyrY at latest landing timing and the preceding landing timing, it is required to collect sensor data for at least two footsteps. Thus, in the present embodiment, operations and effects equivalent to those in the above-described first embodiment can be achieved, and also a left/right landing judgment can be made with a small amount of buffer data, which makes it possible to quickly perform judgment processing with a reduce processing load.

In the present embodiment, whether a landed foot is the left foot or the right foot is judged based on a magnitude relation of the value GY (t) of Y-axis angular velocity data GyrY at latest landing timing with respect to the average value GYav of Y-axis angular velocity data GyrY acquired in a specific period. However, the present invention is not limited thereto. In the present invention, whether a landed foot is the left foot or the right foot may be judged based on a magnitude relation of the value GY(T) of the Y-axis angular velocity data GyrY at the latest landing timing with respect to a predetermined threshold set in advance, in place of the average value GYav of the Y-axis angular velocity data GyrY. Here, the threshold set in advance may be based on the average value of sensor data (Y-axis angular velocity data GyrY) acquired in the user's previous running exercises or may be estimated based on the tendency of temporal changes in the average value.

In the present embodiment as well, a likelihood indicating the stability and correctness of results of left/right landing judgment processing may be set and, based on the likelihood, a method of displaying an exercise index on the display section 220 of the wrist device 200 may be changed, as with the above-described modification example of the first embodiment. In the present embodiment, this likelihood is set based on, for example, the ratio of the value GY(T) of Y-axis angular velocity data GyrY at latest landing timing with reference to the average value GYav of Y-axis angular velocity data GyrY or a threshold set prior to left/right landing judgment processing.

Third Embodiment

Next, an exercise support device according to a third embodiment of the present invention is described with reference to the drawings.

Figure 12:
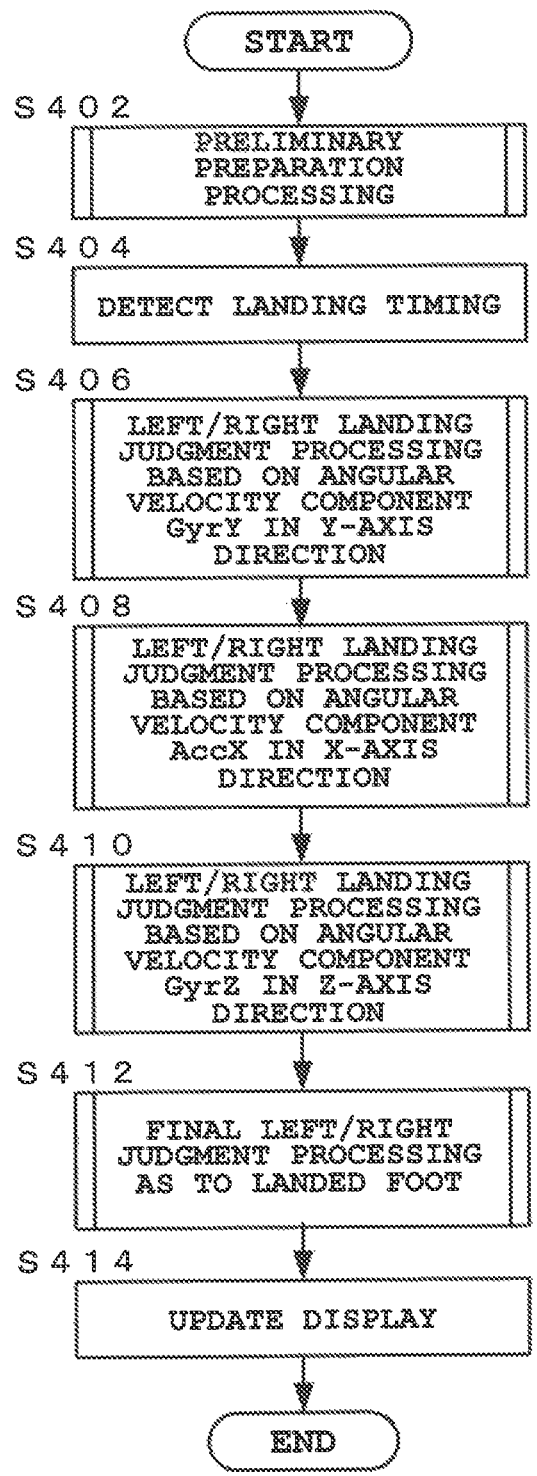
FIG. 12 is a flowchart of one example of an exercise support method according to a third embodiment.
Figure 13:
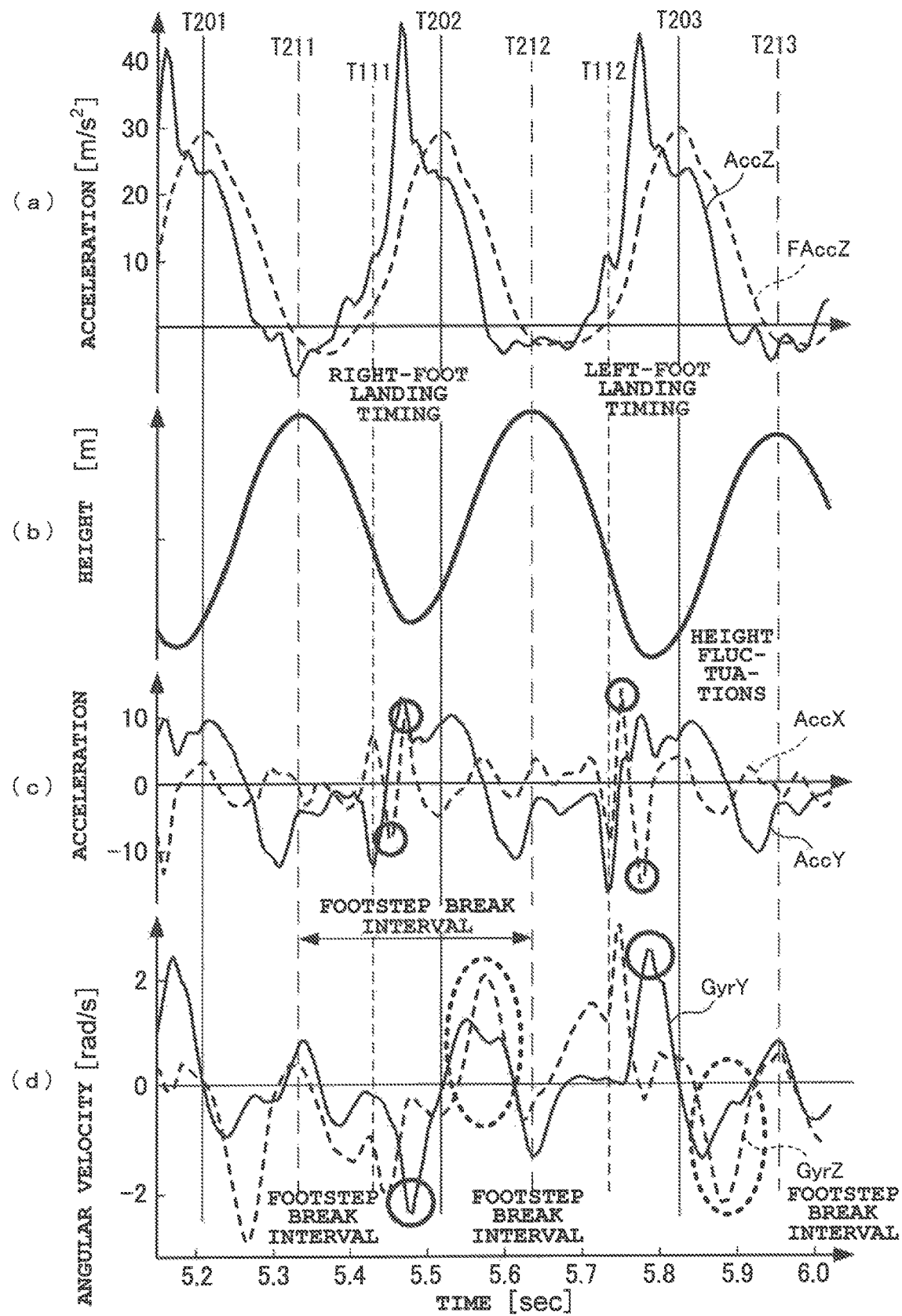
FIG. 13 is a diagram of actually-measured waveforms showing one example of acceleration data acquired by an acceleration measuring section and angular velocity data acquired by an angular velocity measuring section according to the third embodiment.
Figure 14:
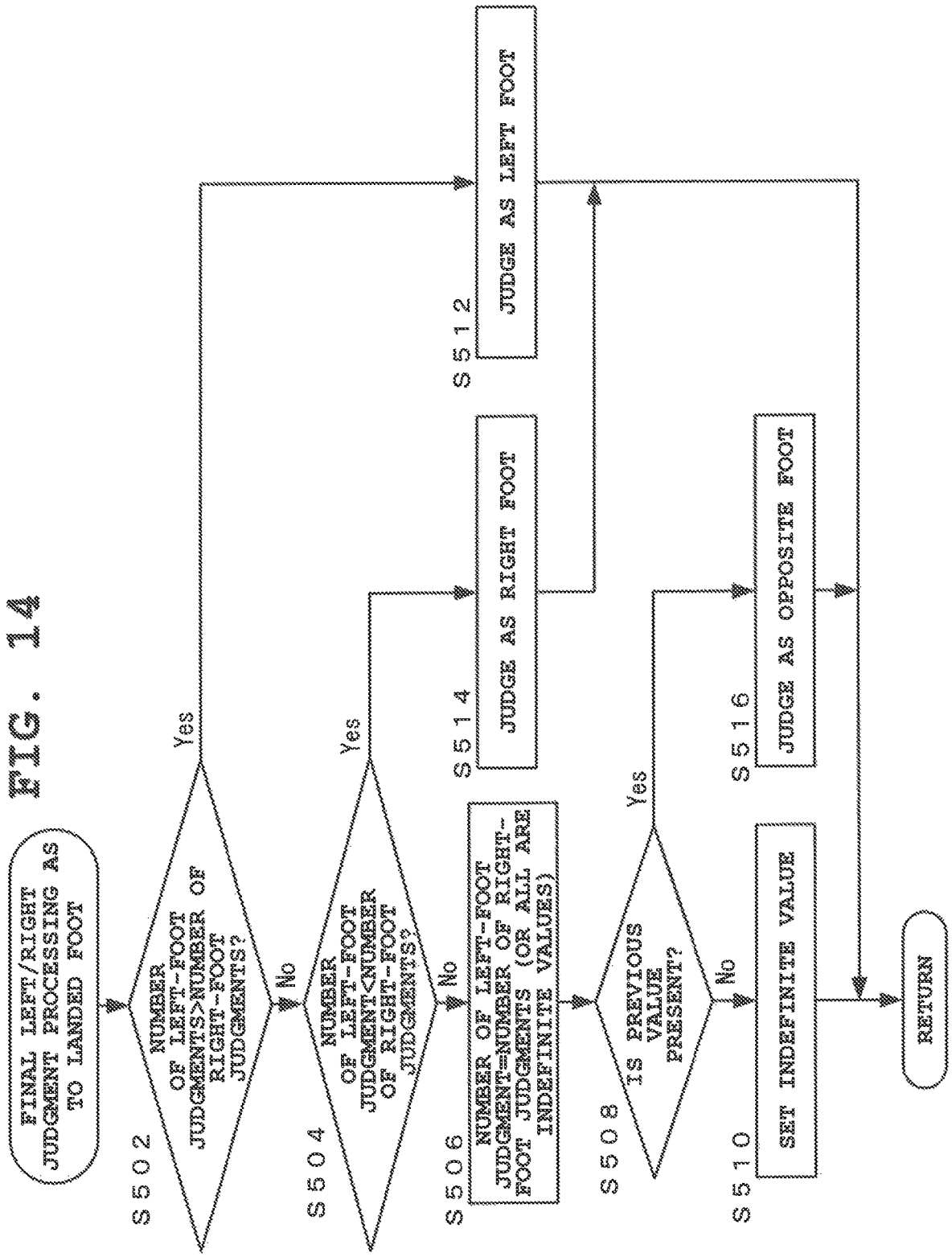
FIG. 14 is a flowchart of one example of final processing in left/right landing judgment processing applied in the exercise support method according to the third embodiment.

FIG. 12 is a flowchart of one example of an exercise support method according to the third embodiment. FIG. 13 is a diagram of actually-measured waveforms showing one example of acceleration data acquired by an acceleration measuring section and angular velocity data acquired by an angular velocity measuring section according to the present embodiment. FIG. 14 is a flowchart of one example of final processing in left/right landing judgment processing applied in the exercise support method according to the present embodiment. Here, processing operations equivalent to those in the above-described first or second embodiment and modification example thereof are described in a simplified manner.

In the above-described first embodiment, whether a landed foot is the left foot or the right foot is judged based on Y-axis angular velocity data GyrY acquired immediately after landing timing (strictly, changes in Y-axis angular velocity data due to the rotating motion of the body occurring after landing). The third embodiment has a feature in which left/right landing judgment processing is performed by a plurality of different methods by using acceleration data or angular velocity data, and whether a landed foot is the left foot or the right foot is finally judged by using a combination of the results of the judgment processing.

In the exercise support method according to the third embodiment, preliminary preparation processing for detecting a break between footsteps based on sensor data acquired during a running exercise is first performed (Step S402), as depicted in the flowchart of FIG. 12. Specifically, when starting a running exercise, the user US operates the wrist device 200, whereby a control signal for instructing to start a sensing operation is transmitted to the sensor device 100 to activate the acceleration measuring section 110 and the angular velocity measuring section 120, and a sampling operation is started. Pieces of sensor data (acceleration data and angular velocity data) acquired by the acceleration measuring section 110 and the angular velocity measuring section 120 are stored in a ring buffer, and a break between left and right footsteps during the running exercise is detected by the signal processing section 150.

The waveform of Z-axis acceleration data AccZ among the acceleration data acquired by the acceleration measuring section 110 during the running exercise is shown as drawing (a) of FIG. 13, and the waveform of X-axis acceleration data AccX and the waveform of Y-axis acceleration data AccY are shown as drawing (c) of FIG. 13. Also, the waveform of Y-axis angular velocity data GyrY and the waveform of Z-axis angular velocity data GyrZ among the angular velocity data acquired by the angular velocity measuring section 120 are shown as drawing (d) of FIG. 13.

With acceleration data and angular velocity data for at least one footstep being acquired, the signal processing section 150 performs smoothing filtering processing such as moving averaging on the Z-axis acceleration data AccZ depicted in drawing (a) of FIG. 13, and calculates smoothed acceleration data FAccZ, as depicted in drawing (a) of FIG. 13. The waveform of this smoothed acceleration data FAccZ corresponds to the Z-axis acceleration data AccZ after smoothing filtering processing depicted in FIG. 6 and drawing (a) of FIG. 8 in the above-described first embodiment.

Next, the signal processing section 150 extracts time points T201, T202, T203, and so on when the smoothed acceleration data FAccZ has a maximum value, and twice integrates acceleration data AccZ between the time points T201 and T202, between the time points T202 and T203, between the time points T203 . . . , whereby data indicating height fluctuations is calculated as depicted in drawing (b) of FIG. 13.

Next, the signal processing section 150 extracts time points T211, T212, T213, and so on when height fluctuation data has a maximum value, and sets these time points as times of breaks in left and right footsteps, as depicted in drawing (b) of FIG. 13. Here, in FIG. 13, for convenience of the drawing, only acceleration data and angular velocity data from a time 5.2 seconds to 6.0 seconds are depicted. However, as a matter of course, in the processing of detecting breaks in footsteps, data at times (for example, times after 6.0 seconds) before and after the times depicted in the drawing are also used.

Note that the preliminary preparation processing applied in the present embodiment is not limited to the method where the times of breaks in footsteps are calculated by the above-described Z-axis acceleration data AccZ being smoothed and then the resultant data being integrated twice. Alternatively, the footstep judgment processing described in the first embodiment may be applied.

Next, the signal processing section 150 detects timing at which either one of the left and right feet is landed during the running exercise (Step S404). Specifically, for example, the signal processing section 150 extracts time points when the Y-axis acceleration data AccY has a negative peak value during a period in which the smoothed acceleration data FAccZ tends to increase, and sets the detected time points as landing timings T111, T112, and so on, as depicted in drawing (c) of FIG. 13. Here, the period in which the smoothed acceleration data FAccZ tends to increase corresponds to a first half of each of periods between the time points T211 and T212, between the time points T212 and T213, between the time points T213, . . . which are the times of breaks in footsteps, as depicted in drawing (b) of FIG. 13. Based on the negative peak of Y-axis acceleration data AccY during each of these periods in which the smoothed acceleration data FAccZ tends to increase, the landing timings T111, T112, and so on are set. Also, as another method for detecting landing timings, for example, the method described in the first embodiment (refer to FIG. 8) may be adopted, and a time point shortly before a time point where the Z-axis acceleration data AccZ after smoothing filter processing exceeds the acceleration of gravity (9.8 m/s$^2$) may be set as landing timing.

Next, by using a specific data component among the sensor data acquired by the acceleration measuring section 110 and the angular velocity measuring section 120, the signal processing section 150 performs left/right landing judgment processing for judging left/right landing by a plurality of different methods. That is, in the present embodiment, left/right landing judgment processing is performed by a method using Y-axis angular velocity data GyrY (first component), a method using X-axis acceleration data AccX (first component), and a method using Z-axis angular velocity data GyrZ (first component). Note that the left/right landing judgment processing by these three methods may be performed concurrently or in time series. In addition, the processing order is not particularly limited. The results of the left/right landing judgment processing are stored in a predetermined storage area of the storage section 140. In the following descriptions, the left/right landing judgment processing by each method is specifically explained.

In left/right landing judgment processing by a first method, based on Y-axis angular velocity data GyrY in a certain time range from the landing timing detected by the above-described landing timing detection processing (Step S404), the signal processing section 150 performs left/right landing judgment processing (Step S406). Specifically, as depicted in drawing (d) of FIG. 13, the signal processing section 150 detects an extreme value (indicated by a solid circle in the drawing) of Y-axis angular velocity data GyrY in a certain time range from each of the above-described landing timings T111, T112, and so on, such as a period of 70 msec. Then, based on whether the extreme value is a positive or negative value, the signal processing section 150 judges whether the current landed foot is the left foot or the right foot. When the extreme value of the Y-axis angular velocity data GyrY is a positive value, the signal processing section 150 judges that the foot landed at that timing is the left foot. On the other hand, when the extreme value of the Y-axis angular velocity data GyrY is a negative value, the signal processing section 150 judges that the foot landed at that timing is the right foot. Here, when no extreme value of the Y-axis angular velocity data GyrY is detected in the certain time range from each of the landing timings T111, T112, and so on, the signal processing section 150 sets the landing judgment results as indefinite values.

That is, in a human body during a running exercise, in order to mitigate impacts by the landing of a foot, the pelvis momentarily moves downward at the time of the landing, and then returns to its original position. For example, when the left foot is landed, a phenomenon occurs in which Y-axis angular velocity data GyrY significantly fluctuates in a plus direction, and then returns to its original position. When the right foot is landed, a phenomenon occurs in which the Y-axis angular velocity data GyrY significantly fluctuates in the minus direction, and then returns to its original position. Therefore, a left/right landing judgment can be made based on whether an extreme value of Y-axis angular velocity data GyrY acquired immediately after landing timing is positive or negative.

In the above-described first embodiment as well, the left/right landing judgment processing is applied based on a technical idea similar to this idea. In the first embodiment, the left/right landing judgment processing is performed based on whether a difference (parameter D) between Y-axis angular velocity data GyrY acquired immediately after latest landing timing and the preceding (immediately preceding) landing timing has a positive or negative value. In general, in running motions, if the way of running or the running speed varies, the tendency of changes in Y-axis angular velocity data GyrY acquired immediately after landing timings may vary (for example, the above-described fluctuations may be delayed). Therefore, in the method of the first embodiment where the value of Y-axis angular velocity data GyrY immediately after landing timing is used, if a difference that allows a judgment regarding the left and right feet cannot be acquired, accuracy in a landed foot judgment may be slightly decreased. Thus, in the present embodiment, the method is adopted in which a positive or negative extreme value of Y-axis angular velocity data GyrY acquired immediately after landing timing is used, whereby accuracy in left/right landing judgment can be more improved.

In left/right landing judgment processing by a second method, based on X-axis acceleration data AccX in a certain time range from the landing timing detected by the above-described landing timing detection processing (Step S404), the signal processing section 150 performs left/right judgment processing (Step S408). Specifically, as depicted in drawing (c) of FIG. 13, the signal processing section 150 detects extreme values (indicated by solid circles in the drawing) of X-axis acceleration data AccX in a certain time range from each of the landing timings T111, T112, and so on, such as a period of 70 msec. Then, in the time range, the plurality of extreme values are detected and, if first two extreme values immediately after the landing timings T111, T112, and so on are in the order of a positive value and then a negative value, the signal processing section 150 judges that the foot landed at that timing is the left foot. On the other hand, if these two extreme values are in the order of a negative value and then a positive value, the signal processing section 150 judges that the foot landed at that timing is the right foot. Here, when only one extreme value of the X-axis acceleration data AccX is detected in the certain time range from the landing timings T111, T112, and so on, and the detected extreme value is a positive value, the signal processing section 150 judges that the landed foot is the left foot. When the detected extreme value is a negative value, the signal processing section 150 judges that the landed foot is the left foot.

That is, in a human body during a running exercise, when a foot is landed, the pelvis moves in a direction of the foot opposite to the landed foot, and then returns to its original position. For example, when the left foot is landed, a phenomenon occurs in which X-axis acceleration data AccX significantly fluctuates in a plus direction, rapidly fluctuates in the minus direction, and then returns to its original position. When the right foot is landed, a phenomenon occurs in which the X-axis acceleration data AccX significantly fluctuates in the minus direction, rapidly fluctuates in the plus direction, and then returns to its original position. Therefore, a left/right landing judgment can be made based on whether an extreme value of X-axis acceleration data AccX acquired immediately after landing timing is positive or negative.

In left/right landing judgment processing by a third method, based on Z-axis angular velocity data GyrZ in a certain time range traced back in time from the break between the footsteps detected by the above-described preliminary preparation processing (Step S402), the signal processing section 150 performs left/right judgment processing (Step S410). Specifically, as depicted in drawing (d) of FIG. 13, the signal processing section 150 integrates angular velocity data GyrZ (indicated by dotted circles in the drawing) in a certain time range traced back in time from each of the times (time points T211, T212, T213, . . . ) of the breaks in the user's steps, and judges whether the current landed foot is the left foot or the right foot based on whether the integrated value is a positive or negative value. Here, the certain time range traced back in time from a time of a break between footsteps is set as a latter half of each of periods between the time points T211 and T212, between the time points T212 and T213, between the time points T213, . . . (for example, a period after 60% to 90% of the period between the time points has elapsed from each of the time points T211, T212, T213, and so on). When the integrated value of the Z-axis angular velocity data GyrZ is a positive value, the signal processing section 150 judges that the foot landed at that timing is the left foot. On the other hand, when the integrated value of the Z-axis angular velocity data GyrZ is a negative value, the signal processing section 150 judges that the foot landed at that timing is the right foot. Here, in the certain time range traced back in time from each of the times (time points T211, T212, T213, . . . ) of the breaks in the user's steps, when the integrated value of the Z-axis angular velocity data GyrZ is 0 (zero), the signal processing section 150 judges that the result of the judgment regarding the landed foot has an indefinite value.

That is, in a human body during a running exercise, when one foot is landed and then the other foot is swung up forward (taken off the ground), the upper half of the body moves to twist in an opposite direction of the body axis with respect to the lower half of the body. For example, when the left foot is landed, a phenomenon occurs in which Z-axis angular velocity data GyrZ fluctuates in a plus direction in a certain time range before the foot is taken off the ground at timing at which the person twists the upper half of the body, and then returns to its original position. When the right foot is landed, a phenomenon occurs in which the Z-axis angular velocity data GyrZ fluctuates in the minus direction in a certain time range before the foot is taken off the ground at timing at which the person twists the upper half of the body, and then returns to its original position. Therefore, a left/right landing judgment can be made based on whether the integrated value of Z-axis angular velocity data GyrZ acquired in a certain time range before a time (timing at which a foot is taken off the ground) of a break between footsteps is a positive or negative value.

Next, based on the results of the left/right landing judgment processing by the plurality of different methods (Steps S406 to S410), the signal processing section 150 performs final left/right judgment processing of finally making a left/right landing judgment (Step S412). In the final left/right judgment processing according to the present embodiment, the control section 160 controls the signal processing section 150 to first judge, from the result of the left/right landing judgment processing by the three methods, whether the number of judgments that a landed foot is the left foot (the number of left-foot judgments) is larger than the number of judgments that a landed foot is the right foot (the number of right-foot judgments) (Step S502), as depicted in the flowchart of FIG. 14. When the number of left-foot judgments is larger than the number of right-foot judgments (Yes at Step S502), the signal processing section 150 finally judges that a landed foot is the left foot (Step S512), ends the final left/right judgment processing, and returns to the flowchart depicted in FIG. 12.

On the other hand, when the number of left-foot judgments is not larger than the number of right-foot judgments (No at Step S502), the signal processing section 150 judges whether the number of left-foot judgments is smaller than the number of right-foot judgments (Step S504). When the number of left-foot judgments is smaller than the number of right-foot judgments (Yes at Step S504), the signal processing section 150 finally judges that a landed foot is the right foot (Step S514), ends the final left/right judgment processing, and returns to the flowchart depicted in FIG. 12.

On the other hand, when the number of left-foot judgments is not smaller than the number of right-foot judgments (No at Step S504), the signal processing section 150 judges that the number of left-foot judgments is equal to the number of right-foot judgments or all results in the judgment processing have indefinite values (Step S506). In this case, the signal processing section 150 judges whether the value of the number of left-foot or right-foot judgments in the preceding final left/right judgment processing is present (Step S508). When the value of the number of left-foot or right-foot judgments in the preceding processing is present (Yes at Step S508), the signal processing section 150 finally judges that the foot opposite to the foot judged last time is the current landed foot (Step S516), ends the final left/right judgment processing, and returns to the flowchart depicted in FIG. 12.

On the other hand, when the number of left-foot or right-foot judgments in the preceding processing is not present (No at Step S508), the signal processing section 150 sets the result of the judgment processing as an indefinite value (Step S510), ends the final left/right judgment processing, and returns to the flowchart depicted in FIG. 12. The result of the final left/right judgment processing is stored in a predetermined storage area of the storage section 140. In addition, the signal processing section 150 disables the angular velocity measuring section 120 when ending the final left/right judgment processing, as with the above-described first embodiment.

Next, the control section 160 transmits at least the judgment result acquired in the above-described final left/right judgment processing (Step S412) to the wrist device 200. As a result, various data regarding the movements of the left and right feet during the running exercise are displayed on the display section 220 of the wrist device 200 as exercise indexes in substantially real time so as to be provided to the user US (Step S414).

In the above-described final left/right judgment processing (Step S412), when the number of left-foot judgments is equal to the number of right-foot judgments as a result of the left/right landing judgment processing by the three methods, the current landed foot is finally judged based on the values of the number of left-foot judgments and the number of right-foot judgments in the preceding final left/right judgment processing. However, the present invention is not limited thereto. In the present invention, when the number of left-foot judgments is equal to the number of right-foot judgments, the current landed foot may be finally judged based on not only the value of the number of judgments in the immediately preceding final left/right judgment processing but also the values of the number of judgments in final left/right judgment processing in a plurality of previous exercises, by which the stability and correctness of the judgment result in the final left/right judgment processing can be improved.

As such, in the present embodiment, left/right landing judgment processing is performed by the plurality of different methods by use of acceleration data or angular velocity data, and whether a landed foot is the left foot or the right foot is finally judged based on a combination of the results of the judgment processing (or majority decision). Here, in the present embodiment, as methods for left/right landing judgment processing, the method based on a judgment as to whether the extreme value of Y-axis angular velocity data GyrY acquired immediately after landing timing during a running exercise is positive or negative, the method based on a judgment as to whether the successive extreme values of X-axis acceleration data AccX acquired immediately after the landing timing are positive or negative, and the method based on a judgment as to whether the integrated value of Z-axis angular velocity data GyrZ acquired in a certain period before the foot is taken off the ground are applied.

As a result of this configuration, even in a case where the tendency of changes in Y-axis angular velocity data GyrY varies due to variations in the way of running or the running speed in a running exercise and the result of left/right landing judgment processing is affected thereby, the exercise support device according to the present embodiment performs left/right landing judgment processing by the plurality of different methods, and makes a left/right landing judgment comprehensively based on the judgment result, whereby an accurate exercise index can be provided to the user with improved accuracy in the landing judgment.

In the present embodiment, in the above-described left/right landing judgment processing by the three methods (Steps S406 to S410), a left/right landing judgment during a running exercise is made only with sensor data for one footstep serving as a judgment target. However, the present invention is not limited thereto. In the present invention, for example, sensor data for at least two footsteps may be collected as described in the first embodiment, and a left/right landing judgment may be made by using a difference between sensor data acquired before and after the landing timings of successive two footsteps.

Also, in the present embodiment, in each left/right landing judgment processing by the three methods (Steps S406 to S410), whether a landed foot is the left foot or the right foot is judged. Then, in the final left/right judgment processing (Step S412), the landed foot is finally judged based on a majority decision as to the judgment results (the left foot, the right foot, or an indefinite value). However, the present invention is not limited thereto. In the present invention, a configuration may be adopted in which, in each left/right landing judgment processing by the three methods, a likelihood indicating the stability and correctness of a judgment result is calculated as described in the modification example of the first embodiment, and the calculated likelihood values are compared so as to make a final judgment as to the landed foot.

Fourth Embodiment

Next, an exercise support device according to a fourth embodiment of the present invention is described with reference to the drawings.

Figure 15:
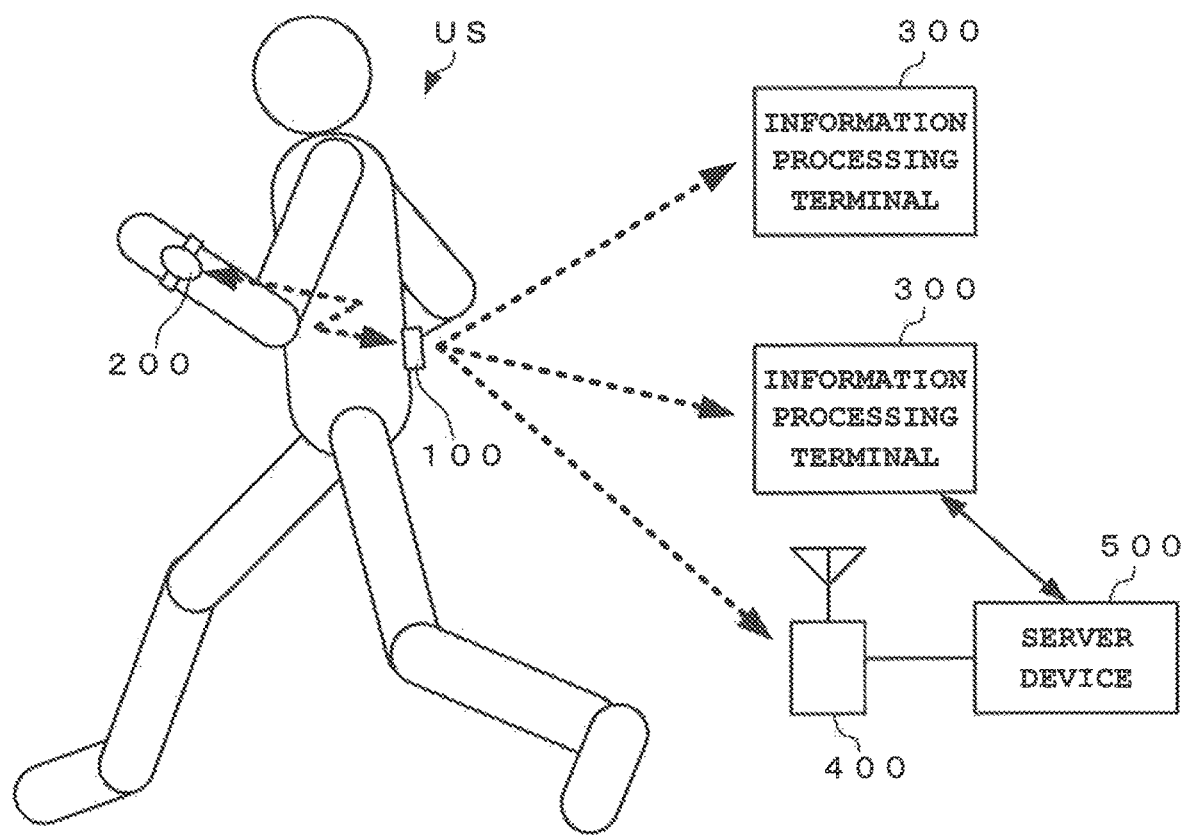
FIG. 15 is a schematic diagram showing an exercise support device according to a fourth embodiment of the present invention.
Figure 16:
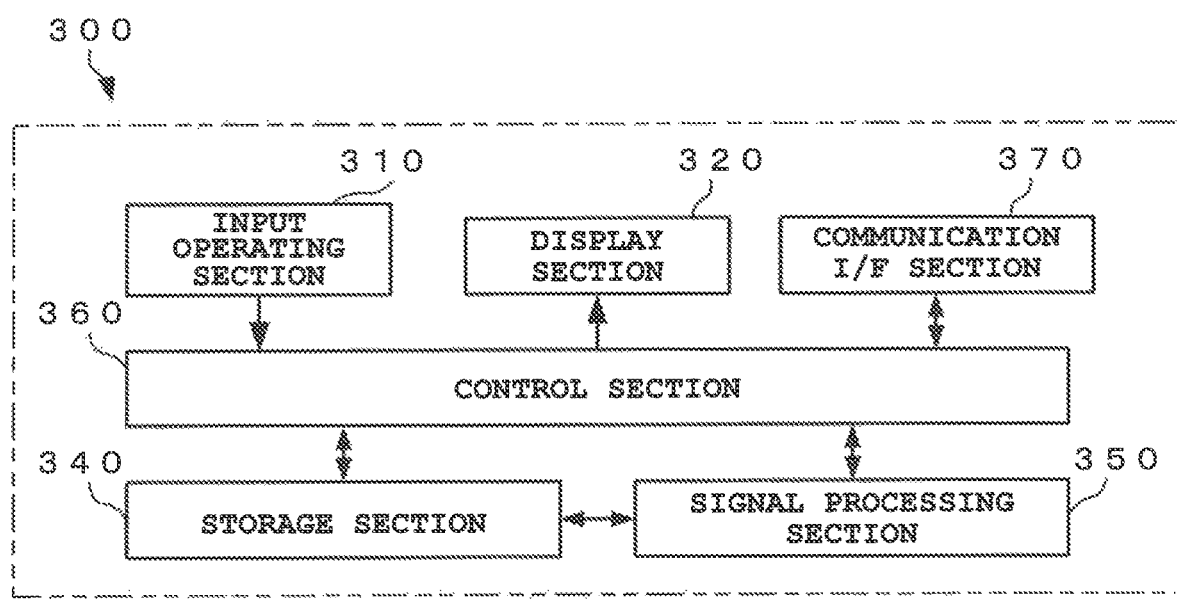
FIG. 16 is a functional block diagram showing the structure of an information processing terminal applied in the exercise support device according to the fourth embodiment.
Figure 17:
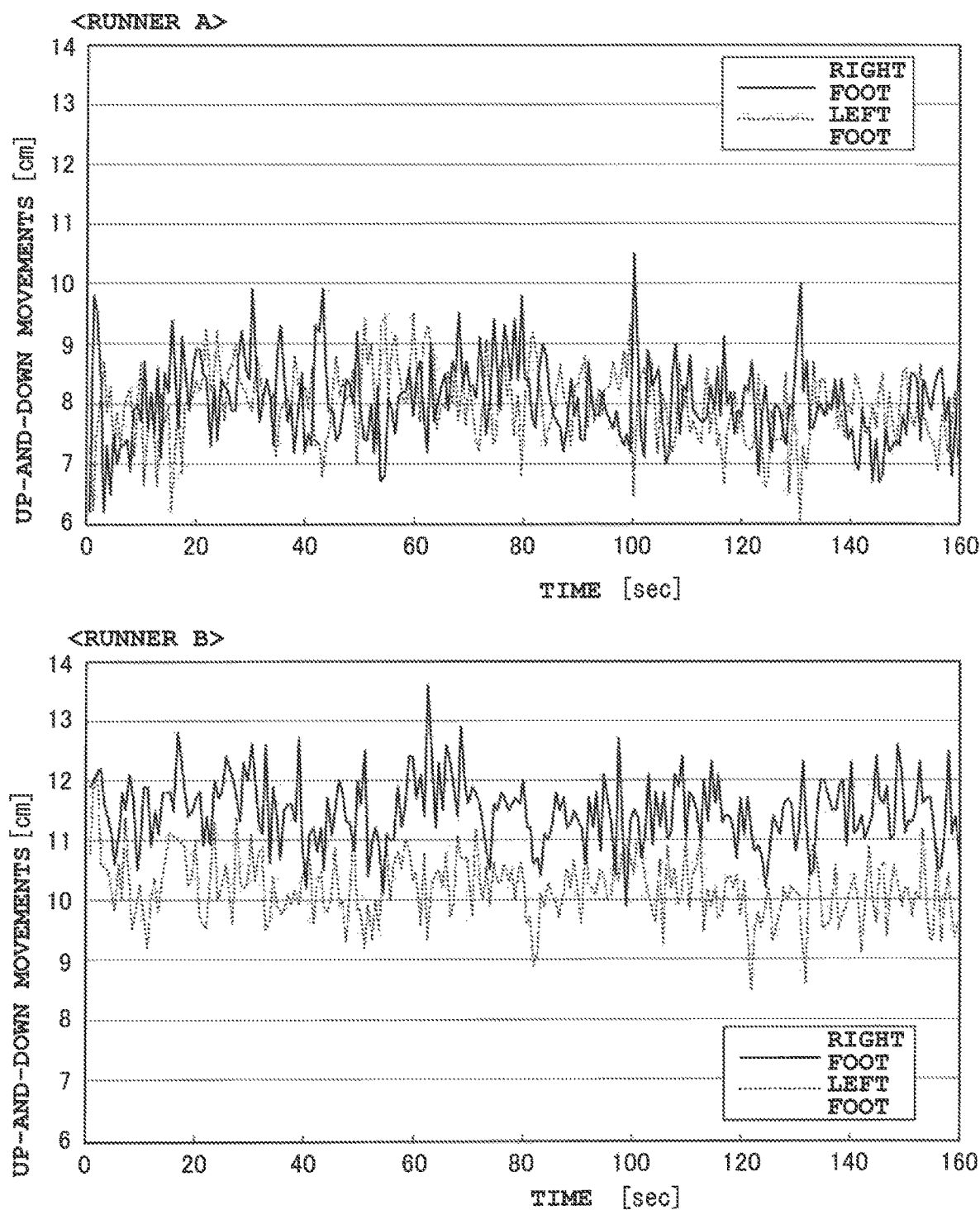
FIG. 17 is a diagram of a display example of exercise indexes in the information processing terminal applied in the fourth embodiment.

FIG. 15 is a schematic diagram of the exercise support device according to the fourth embodiment of the present invention, and FIG. 16 is a functional block diagram showing the structure of an information processing terminal applied in the exercise support device according to the present embodiment. FIG. 17 is a diagram showing a display example of exercise indexes in the information processing terminal applied in the present embodiment. Note that processing operations equivalent to those in the above-described first to third embodiments are described in a simplified manner.

In the above-described first to third embodiments, sensor data during a running exercise is acquired by the sensor device 100, processing for judging a landed foot is performed based on the sensor data, the judgment result is transmitted to the wrist device 200, and a predetermined exercise index is provided to the user in real time. The fourth embodiment has a feature in which sensor data during a running exercise is collected by the sensor device 100, the sensor data is transmitted to an external device (such as an information processing terminal or server device) after the end of the running exercise, processing for judging a landed foot is performed by the external device, and a predetermined exercise index is provided to the user.

The exercise support device according to the fourth embodiment has, for example, a sensor device 100, a wrist device 200, and an information processing terminal 300, as depicted in FIG. 15. Here, in the structure depicted in each embodiment described above (refer to FIG. 2A), the sensor device 100 has at least a function of sequentially storing sensor data acquired during a running exercise in the storage section 140 in association with time data and a function of transmitting and receiving various signals and data to and from the information processing terminal 300 that is an external device in addition to the wrist device 200, by the communication I/F section 170. That is, the sensor device 100 has a function for serving as a data logger, and is not required to have the function for performing the processing of judging a landed foot or the processing of calculating an exercise index based on sensor data acquired during a running exercise by the signal processing section 150 described in each embodiment.

Also, the wrist device 200 has the structure depicted in each embodiment (refer to FIG. 2B) and has at least a function for giving an instruction to start or end a sensing operation in the sensor device 100 by the user US operating the input operating section 210. That is, the wrist device 200 is not required to have a function of displaying various data regarding an exercise status calculated based on sensor data acquired by the sensor device 100 and the like.

The information processing terminal 300 is an electronic device capable of transmitting and receiving various signals and data to and from at least the sensor device 100 by a predetermined communication method and displaying various data and the like regarding an exercise status including an exercise index calculated based on sensor data received from the sensor device 100. As the information processing terminal 300, for example, a general-purpose device such as a notebook or desktop personal computer, a smartphone, or a tablet terminal, or a dedicated device is applied.

Specifically, the information processing terminal 300 includes, for example, an input operating section 310, a display section 320, a storage section 340, a signal processing section 350, a control section 360, and a communication I/F section 370, as depicted in FIG. 16.

The input operating section 310 is input means annexed to the information processing terminal 300, such as a keyboard, a mouse, a touchpad, or a touch panel. This input operating section 310 is used for an input operation for causing desired information and the like to be displayed on the display section 320 and for performing various types of processing and setting. The display section 320 has a display panel of, for example, a liquid-crystal type or light-emitting-element type, and displays at least information regarding an input operation by the input operating section 210, a communication status with the sensor device 100, various data regarding an exercise status calculated based on sensor data transmitted from the sensor device 100, and the like in a predetermined format. Here, the display section 320 preferably has a high-definition display panel having a large screen size as compared to the display section 220 applied in the wrist device 200 that is worn on a human body.

The storage section 340 stores, in a predetermined storage area, sensor data acquired during a running exercise and transmitted from the sensor device 100 via the communication I/F section 370 described later. Also, by the signal processing section 350 and the control section 360 executing a predetermined control program and algorithm program, the storage section 340 stores, in a predetermined storage area, various data regarding an exercise status including an exercise index calculated based on sensor data and the like. Note that the storage section 340 may be partially or entirely in a form of a removable storage medium, and may be structured to be removable from the information processing terminal 300.

The signal processing section 350 judges a landed foot based on sensor data transmitted from the sensor device 100 in accordance with an instruction from the control section 360, and calculates various data regarding the exercise status of the user US including an exercise index indicating a left/right balance in the use of the body in an exercise.

The control section 360 is an arithmetic processing device having a clock function. By executing a predetermine control program, the control section 360 controls an operation of displaying various data and the like on the display section 220, an operation of storing and reading various data and the like in the storage section 340, an operation for communication by the communication I/F section 370 with the sensor device 100, and the like. Also, by executing a predetermined algorithm program, the control section 360 controls predetermined signal processing in the signal processing section 350, such as judgment as to a landed foot and calculation of an exercise index and the like. Here, as the arithmetic processing device applied in the control section 360, a device having high arithmetic processing performance as compared to the arithmetic processing device applied in the sensor device 100 and the wrist device 200 that are worn on a human body should preferably be applied. Since signal processing to be performed in the signal processing section 350 and the control section 360 is equivalent to that in the exercise support method described in each of the above embodiments, specific description is omitted. Also, the communication I/F section 370 at least communicates with the sensor device 100, and receives sensor data acquired during a running exercise.

In the present embodiment, in the exercise support device structured as described above, sensor data collected by the sensor device 100 during a running exercise is transmitted from the sensor device 100 to the information processing terminal 300 after the running exercise. Then, based on the received sensor data, the signal processing section 350 and the control section 360 of the information processing terminal 300 perform detailed and various analysis processing including predetermined signal processing such as judgment as to a landed foot and calculation of an exercise index as in the case of the exercise support method described in each embodiment, and cause various data regarding the exercise status of the user US to be displayed on the display section 320 in a predetermined format.

Specifically, various data regarding the exercise status are displayed on the display section 320 of the information processing terminal 300 such that changes in a relation between the steps of the left and right feet during the running exercise and the up-and-down movements of the body with time are displayed in a graph format, as depicted in FIG. 17. Here, for example, graphs of different users (for example, runner A and runner B) are displayed by being arranged vertically in parallel on the screen of the display section 320 such that they can be compared with each other. Graphs depicted in upper and lower portions of FIG. 17 represent up-and-down movements of the bodies of runner A and runner B when they are running two laps around a track. According to the display format of various data and the like depicted in FIG. 17, it can be found that runner A has relatively small up-and-down movements of the body and there is almost no difference in up-and-down movements between the left and right feet. By contrast, it can be found that runner B has not only large up-and-down movements of the body but also a large difference in movements between the left and right feet. The display format of various data and the like displayed on the display section 320 is not limited to that depicted in FIG. 17, and a graph and numerical values of various data regarding the training of a specific user on a specific day may be singly displayed, or a graph and numerical values regarding training on a different day may be displayed in parallel.

As such, in the present embodiment, detailed and various analysis processing including signal processing such as judgment as to a landed foot and calculation of an exercise index in the information processing terminal 300 is performed based on sensor data collected by the sensor device 100, and the results are displayed on the high-definition display section 320 with a relatively large screen size in a predetermined format, so that the user can appropriately and multilaterally grasp the balance of the use of the body in the exercise for judgment and improvement.

Also, in the present embodiment, the sensor device 100 is only required to have a function for collecting sensor data during a running exercise, and is not required to have a function for performing signal processing such as judgment as to a landed foot and calculation of an exercise index. Therefore, the processing load on the sensor device can be reduced to prolong its battery driving time, and the device structure of the sensor device 100 can be simplified to decrease the size and weight.

In the present embodiment, sensor data collected during a running exercise by the sensor device 100 is transmitted to the information processing terminal 300, and the information processing terminal 300 performs signal processing such as judgment as to a landed foot and calculation of an exercise index. However, the present invention is not limited thereto. That is, for example, a configuration may be adopted in which sensor data collected during a running exercise by the sensor device 100 is transferred to a server device 500 via the information processing terminal 300 or a network relay device 400, and the server device 500 performs signal processing such as judgment as to a landed foot and calculation of an exercise index, as depicted in FIG. 15.

In this configuration, in addition to a function for transferring at least sensor data transmitted from the sensor device 100 to the server device 500, the information processing terminal 300 is required to have at least a function for connecting to the network and allowing various data regarding the user's exercise status generated by the signal processing in the server device 500 and the like to be viewed. However, the information processing terminal 300 is not required to have a function for performing signal processing such as judgment as to a landed foot and calculation of an exercise index. Also, the network relay device 400 has only a function for transferring sensor data transmitted from the sensor device 100 to the server device 500. Also, the server device 500 has a structure substantially equivalent to the structure of the information processing terminal 300 depicted in FIG. 16, and has at least a function for receiving sensor data transferred via the information processing terminal 300 or the network relay device 400 and a function for performing signal processing such as judgment as to a landed foot and calculation of an exercise index based on the sensor data. As a result of this configuration, the user can view various data regarding an exercise status and the like by accessing the server device 500 by using the information processing terminal 300 having relatively low arithmetic processing capability and a simple structure. That is, the exercise support device according to the present invention can be easily structured at low cost.

While the present invention has been described with reference to the preferred embodiments, it is intended that the invention be not limited by any of the details of the description therein but includes all the embodiments which fall within the scope of the appended claims.

What is claimed is:

1. An exercise support device comprising:
at least one processor; and
a memory storing instructions that, when executed by the at least one processor, control the at least one processor to:
make a determination, by using a first component of sensor data acquired at certain timing that is determined based on landing timing at which one of a left foot and a right foot of a user is landed, whether a foot landed at the landing timing is the left foot of the user or the right foot of the user, the landing timing being determined by the sensor data, the sensor data being detected by a sensor that detects a motion status of the body of the user when the user travels, the sensor having an acceleration measuring function and an angular velocity measuring function, the sensor being configured to output, as part of the sensor data corresponding to the motion status, angular velocity data of a rotating motion around a traveling direction of the user taken as a Y-axis, and the sensor being configured to be worn on a waist, abdomen, chest, or neck of the user;
wherein the instructions further control the at least one processor to:
make the determination by using at least the angular velocity data on the Y-axis outputted from the sensor as the first component of the sensor data; and
after making the determination of whether the foot landed at the landing timing is the left foot of the user or the right foot of the user, disable the angular velocity measuring function of the sensor and monitor whether a fluctuation in time per step is larger than a threshold, and, when the fluctuation in time per step is larger than the threshold, enable the angular velocity measuring function of the sensor and make a subsequent determination whether a foot landed at another landing timing is the left foot of the user or the right foot of the user.

2. The exercise support device according to claim 1,
wherein the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis,
wherein the instructions further control the at least one processor to:
determine the landing timing by using, as a second component of the sensor data, the acceleration data on the Z-axis or the acceleration data on the Y-axis; and
make the determination of whether the foot landed at the landing timing is the left foot of the user or the right foot of the user by making a plurality of sub-determinations, and making, as the determination, a final determination, based on results of the plurality of sub-determinations, and
wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data.

3. The exercise support device according to claim 1,
wherein the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis,
wherein the instructions further control the at least one processor to:
determine the landing timing by using, as a second component of the sensor data, the acceleration data on the Z-axis or the acceleration data on the Y-axis; and
make the determination of whether the foot landed at the landing timing is the left foot of the user or the right foot of the user by making a plurality of sub-determinations, and making, as the determination, a final determination, based on results of the plurality of sub-determinations,
wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data; and
wherein the instructions control the at least one processor to make the final determination of whether the landed foot is the left foot or the right foot of the user based on a comparison between a number of results from among results of the respective sub-determinations which indicate that the landed foot is the right foot of the user and a number of results from among the results of the respective sub-determinations which indicate that the landed foot is the left foot of the user.

4. The exercise support device according to claim 1,
wherein the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis, wherein the instructions further control the at least one processor to:
determine the landing timing by using, as a second component of the sensor data, the acceleration data on the Z-axis or the acceleration data on the Y-axis; and
make the determination of whether the foot landed at the landing timing is the left foot of the user or the right foot of the user by making a plurality of sub-determinations, and making, as the determination, a final determination, based on results of the plurality of sub-determinations,
wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data; and
wherein the instructions control the at least one processor to make the final determination of whether the landed foot is the left foot or the right foot of the user based on likelihoods of results from among results of the respective sub-determinations which indicate that the landed foot is the right foot of the user and likelihoods of results from among the results of the respective sub-determinations which indicate that the landed foot is the left foot of the user.

5. The exercise support device according to claim 1, wherein the instructions further control the at least one processor to:
display an index in a certain format on a display, the index regarding the motion status of the body of the user obtained based on a result of the determination regarding the foot landed.

6. The exercise support device according to claim 1, wherein the instructions further control the at least one processor to:
perform the determination regarding the foot landed a plurality of times; and
display an index in a certain format on a display, the index regarding the motion status of the body of the user obtained based on a plurality of results of the determination which is performed the plurality of times; and
wherein the index is displayed in different formats on the display in accordance with likelihoods of the plurality of results of the determination performed the plurality of times.

7. The exercise support device according to claim 1, further comprising:
the sensor that outputs the sensor data corresponding to the motion status; and
a display that displays an index in a certain format, the index regarding the motion status of the body of the user obtained based on a result of the determination regarding the foot landed.

8. An exercise support method comprising:
making a determination, by using a first component of sensor data acquired at certain timing that is determined based on landing timing at which one of a left foot and a right foot of a user is landed, whether a foot landed at the landing timing is the left foot of the user or the right foot of the user, the landing timing being determined by the sensor data, the sensor data being detected by a sensor that detects a motion status of the body of the user when the user travels, the sensor having an acceleration measuring function and an angular velocity measuring function, the sensor being configured to output, as part of the sensor data corresponding to the motion status, angular velocity data of a rotating motion around a traveling direction of the user taken as a Y-axis, and the sensor being configured to be worn on a waist, abdomen, chest, or neck of the user;
wherein the method further comprises:
making the determination by using at least the angular velocity data on the Y-axis outputted from the sensor as the first component of the sensor data; and
after making the determination of whether the foot landed at the landing timing is the left foot of the user or the right foot of the user, disabling the angular velocity measuring function of the sensor and monitoring whether a fluctuation in time per step is larger than a threshold, and, when the fluctuation in time per step is larger than the threshold, enabling the angular velocity measuring function of the sensor and make a subsequent determination whether a foot landed at another landing timing is the left foot of the user or the right foot of the user.

9. The exercise support method according to claim 8, wherein the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis,
wherein the method further comprises determining the landing timing by using, as a second component of the sensor data, the acceleration data on the Z-axis or the acceleration data on the Y-axis;
wherein making the determination of whether the foot landed at the landing timing is the left foot of the user or the right foot of the user comprises making a plurality of sub-determinations, and making, as the determination, a final determination, based on results of the plurality of sub-determinations, and
wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data.

10. The exercise support method according to claim 8, wherein the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis,
wherein the method further comprises determining the landing timing by using, as a second component of the sensor data, the acceleration data on the Z-axis or the acceleration data on the Y-axis;
wherein making the determination of whether the foot landed at the landing timing is the left foot of the user or the right foot of the user comprises making a plurality of sub-determinations, and making, as the determination, a final determination, based on results of the plurality of sub-determinations,
wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data; and wherein the final determination of whether the landed foot is the left foot or the right foot of the user is made based on a comparison between a number of results from among results of the respective sub-determinations which indicate that the landed foot is the right foot of the user and a number of results from among the results of the respective sub-determinations which indicate that the landed foot is the left foot of the user.

11. The exercise support method according to claim 8,
wherein the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis, wherein the method further comprises:
determining the landing timing by using, as a second component of the sensor data, the acceleration data on the Z-axis or the acceleration data on the Y-axis;
wherein making the determination of whether the foot landed at the landing timing is the left foot of the user or the right foot of the user comprises making a plurality of sub-determinations, and making, as the determination, a final determination, based on results of the plurality of sub-determinations,
wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data; and
wherein the final determination of whether the landed foot is the left foot or the right foot of the user is made based on likelihoods of results from among results of the respective sub-determinations which indicate that the landed foot is the right foot of the user and likelihoods of results from among the results of the respective sub-determinations which indicate that the landed foot is the left foot of the user.

12. A non-transitory computer-readable storage medium storing instructions which, when executed by at least one processor, control the processor to:
make a determination, by using a first component of sensor data acquired at certain timing that is determined based on landing timing at which one of a left foot and a right foot of a user is landed, whether a foot landed at the landing timing is the left foot of the user or the right foot of the user, the landing timing being determined by the sensor data, the sensor data being detected by a sensor that detects a motion status of the body of the user when the user travels, the sensor having an acceleration measuring function and an angular velocity measuring function, the sensor being configured to output, as part of the sensor data corresponding to the motion status, angular velocity data of a rotating motion around a traveling direction of the user taken as a Y-axis, and the sensor being configured to be worn on a waist, abdomen, chest, or neck of the user;

wherein the instructions further control the at least one processor to:
make the determination by using at least the angular velocity data on the Y-axis outputted from the sensor as the first component of the sensor data; and
after making the determination of whether the foot landed at the landing timing is the left foot of the user or the right foot of the user, disable the angular velocity measuring function of the sensor and monitor whether a fluctuation in time per step is larger than a threshold, and, when the fluctuation in time per step is larger than the threshold, enable the angular velocity measuring function of the sensor and make a subsequent determination whether a foot landed at another landing timing is the left foot of the user or the right foot of the user.

13. The non-transitory computer-readable storage medium according to claim 12,
wherein the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis,
wherein the instructions further control the at least one processor to:
determine the landing timing by using, as a second component of the sensor data, the acceleration data on the Z-axis or the acceleration data on the Y-axis; and
make the determination of whether the foot landed at the landing timing is the left foot of the user or the right foot of the user comprises by making a plurality of sub-determinations, and making, as the determination, a final determination, based on results of the plurality of sub-determinations, and
wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data.

14. The non-transitory computer-readable storage medium according to claim 12, wherein:
the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis,
wherein the instructions further control the at least one processor to:
determine the landing timing by using, as a second component of the sensor data, the acceleration data on the Z-axis or the acceleration data on the Y-axis; and
make the determination of whether the foot landed at the landing timing is the left foot of the user or the right foot of the user comprises by making a plurality of sub-determinations, and making, as the determination, a final determination, based on results of the plurality of sub-determinations,
wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data; and wherein the instructions control the at least one processor to make the final determination of whether the landed foot is the left foot or the right foot of the user based on a comparison between a number of results from among results of the respective sub-determinations which indicate that the landed foot is the right foot of the user and a number of results from among the results of the respective sub-determinations which indicate that the landed foot is the left foot of the user.

15. The non-transitory computer-readable storage medium according to claim 12, wherein the sensor further outputs, as other parts of the sensor data, acceleration data on an X-axis orthogonal to the traveling direction and horizontal to ground, acceleration data on the Y-axis, acceleration data on a Z-axis orthogonal to the traveling direction and perpendicular to the ground, and angular velocity data on the Z-axis, wherein the instructions further control the at least one processor to:

determine the landing timing by using, as a second component of the sensor data, the acceleration data on the Z-axis or the acceleration data on the Y-axis; and make the determination of whether the foot landed at the landing timing is the left foot of the user or the right foot of the user comprises by making a plurality of sub-determinations, and making, as the determination, a final determination, based on results of the plurality of sub-determinations, wherein the plurality of sub-determinations comprise a sub-determination made by using the angular velocity data on the Y-axis as the first component of the sensor data, a sub-determination made by using the angular velocity data on the Z-axis as the first component of the sensor data, and a sub-determination made by using the acceleration data on the X-axis as the first component of the sensor data; and wherein the instructions control the at least one processor to make the final determination of whether the landed foot is the left foot or the right foot of the user based on likelihoods of results from among results of the respective sub-determinations which indicate that the landed foot is the right foot of the user and likelihoods of results from among the results of the respective sub-determinations which indicate that the landed foot is the left foot of the user.

16. An exercise support system comprising:

a sensor that detects a motion status of a body of a user when the user travels, the sensor having an acceleration measuring function and an angular velocity measuring function, and the sensor being configured to be worn on a waist, abdomen, chest, or neck of the user;

an exercise support device provided separately from the sensor and comprising:

at least one processor; and a memory storing instructions that, when executed by the at least one processor, control the at least one processor to:

make a determination, by using a first component of sensor data acquired at certain timing that is determined based on landing timing at which one of a left foot and a right foot of a user is landed, whether a foot landed at the landing timing is the left foot of the user or the right foot of the user, the landing timing being determined by the sensor data, the sensor data being detected by the sensor, which outputs, as part of the sensor data corresponding to the motion status, angular velocity data of a rotating motion around a traveling direction of the user taken as a Y-axis;

wherein the instructions further control the at least one processor to:

make the determination by using at least the angular velocity data on the Y-axis outputted from the sensor as the first component of the sensor data; and after making the determination of whether the foot landed at the landing timing is the left foot of the user or the right foot of the user, disable the angular velocity measuring function of the sensor and monitor whether a fluctuation in time per step is larger than a threshold, and, when the fluctuation in time per step is larger than the threshold, enable the angular velocity measuring function of the sensor and make a subsequent determination whether a foot landed at another landing timing is the left foot of the user or the right foot of the user.

17. The exercise support system according to claim 16, further comprising:

a display that displays an index in a certain format, the index regarding the motion status of the body of the user obtained based on at least one result of the determination regarding the foot landed.

* * * * *